United States Patent
Khodabocus et al.

(10) Patent No.: US 7,332,614 B2
(45) Date of Patent: Feb. 19, 2008

(54) PROCESS FOR CROSS COUPLING INDOLES

(75) Inventors: Ahmad Khodabocus, Richmond, VA (US); Guisheng Li, Richmond, VA (US); Zhi-Hui Lu, Glen Allen, VA (US); Frank Roschangar, Glen Allen, VA (US); Chris Hugh Senanayake, Brookfield, CT (US); Ming Shen, Waltham, MA (US)

(73) Assignee: Boehringer Ingelheim International, GmbH, Ingelheim (DE)

( * ) Notice: Subject to any disclaimer, the term of this patent is extended or adjusted under 35 U.S.C. 154(b) by 157 days.

(21) Appl. No.: 11/074,194

(22) Filed: Mar. 7, 2005

(65) Prior Publication Data

US 2005/0234242 A1     Oct. 20, 2005

Related U.S. Application Data

(60) Provisional application No. 60/551,107, filed on Mar. 8, 2004.

(51) Int. Cl.
C07D 209/10 (2006.01)
A61K 31/404 (2006.01)

(52) U.S. Cl. ........................ 548/452; 548/469; 514/415

(58) Field of Classification Search ............ 548/452, 548/469; 514/415
See application file for complete search history.

(56) References Cited

U.S. PATENT DOCUMENTS

2004/0024190 A1    2/2004    Beaulieu et al.

OTHER PUBLICATIONS

Miller, J. A. et al, "Preparation of Unsymmetrical Biaryls via Ni- or Pd-Catalyzed Coupling of Aryl chlorides with Arylzincs". Tetrahdron Letters, vol. 39 (36), 1998, pp. 6441-6444.*
Stanforth, S. P. "Catalytic Cross-coupling Reactions in Biaryl Synthesis" Tetrahedron, vol. 34(3-4), 1998, pp. 272-276.*
Danieli, B., et al. "Application of the Pd-catalyzed heteroarylation to the synthesis of 5-(indol-2'-yl)pyridin-2-one and 5-(indol-2'-yl) pyran-2-one" Tetrahedron, vol. 54, No. 46, 1998, p. 14081 XP004139916.
Mercedes Amat, et al., "An Efficient Synthesis of 2-(2-Pyridyl)indoles by Palladium (0)-catalyzed heteroarylation", Tetrahedron Letters, vol. 34, No. 31, 1993 p. 5005 XP002335849.
Sakamoto, T., et al. "Indolylzinc Iodides by Oxidative addition of active zinc To Iodoindoles" Tetrahedron Letters, vol. 34, No. 37, 1993, p. 5955 XP001109072.
Miller, J. A., et al. "Preparation of Unsymmetrical Biaryls via Ni- or Pd-Catalyzed Coupling of Aryl chlorides with Arylzincs" Tetrahedron Letters, vol. 39, No. 36, 1998, p. 6441 XP004132514.
Akio Minato, et al. "Palladium-Phosphine Complex Catalyzed Cross-Coupling Reaction of 1-Methyl-2-pyrrolyl-magnesium Bromide and -zinc chloride with organic halides" Tetrahedron Letters vol. 22, No. 52, 1981 p. 5319 XP002335850.
Stanforth, S.P., "Catalytic Cross-coupling Reactions in Biaryl Synthesis" Tetrahedron, vol. 54, No. 3-4, 1998, p. 263.

* cited by examiner

Primary Examiner—Kamal A. Saeed
Assistant Examiner—Janet L. Coppins
(74) Attorney, Agent, or Firm—Michael Morris; Mary-Ellen M. Devlin; David Dow

(57) ABSTRACT

The present invention provides a process for making a compound of general formula I:

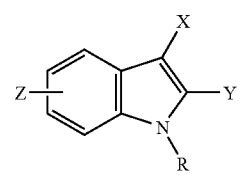

wherein:
R=H or $C_{1-8}$alkyl
X=$C_3$-$C_8$cycloalkyl, $C_3$-$C_8$aryl or $C_3$-$C_8$alkyl;
Y=heteroaryl or aryl;
Z=H, $HO_2C$—, $C_{1-8}$alkyl $O_2C$—, $C_{1-6}$alkyl HNC(O)—,

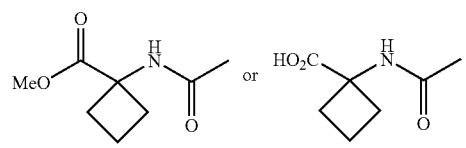

and as described herein.

13 Claims, No Drawings

PROCESS FOR CROSS COUPLING INDOLES

RELATED APPLICATIONS

This application claims priority to U.S. provisional patent application No. 60/551,107 filed Mar. 8, 2004 the contents of which are incorporated herein.

FIELD OF THE INVENTION

The invention relates to the field of pharmaceuticals and more specifically to processes for making 2,3-disubstituted indoles.

BACKGROUND OF THE INVENTION

Substituted indoles are useful as pharmaceutical agents. Examples of substituted indoles used as pharmaceutical agents and the preparation thereof include the anti-inflammatory agents indomethacin and tropesin, the antihistamine mebhydroline, and the vasodilator vinpocetine. Other examples of indole compounds used as pharmaceutical agents are indole compounds such as disclosed in U.S. patent application Ser. No. 10/198,384 (US2004/0024190) the contents of which are incorporated herein by reference and useful as HCV polymerase inhibitors in the treatment of HCV infections.

A convenient method for preparing aryl-substituted indoles is by a palladium catalyzed cross coupling reaction, such as for example Negishi cross coupling (E. Negishi, S. Baba, *J. Chem. Soc. Chem. Communications*, 1976, 596-597; S. Baba, E. Negishi, *J. Am. Chem. Soc.*, 1976, 98, 6729-6731), or Suzuki cross coupling (J. Hassan et al., *Chem Rev.*, 2002, 102, 1359 and N. Miyaura and A. Suzuki, *Chem. Rev.*, 1995, 95, 2457). The methodology of Negishi coupling was developed for $Csp^2$-$Csp^2$ or $Csp^2$-$Csp$ bond formation between alkenyl or aryl halides and organometallic reagents including organoaluminum and organozinc reagents ($Csp^2$ or $Csp$) via palladium-catalyzed cross coupling (Scheme I).

Scheme I

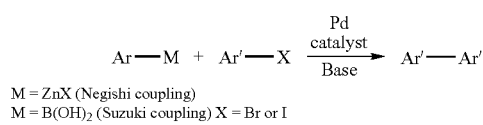

M = ZnX (Negishi coupling)
M = B(OH)₂ (Suzuki coupling) X = Br or I

Cross coupling reactions have been known to have substrate requirements, possibly as a result of the steric and electronic demand of catalysts. Because of the substrate requirements there are no uniform optimal conditions suitable for a broad range of substrates. Therefore, extensive screening of variables and their combinations is often necessary to develop a practical and economical manufacturing process using this methodology. Important variables often include, but are not limited to selection of metal catalysts, such as Pd, Ni, Pt etc, ligands, such as mono-dentate triphenylphosphine ($Ph_3P$), tri-p-tolylphosphine ($p$-$Tol_3P$), tricyclohexylphosphine ($PCy_3$), tri-t-butylphosphine ($t$-$Bu_3P$), ($Cy_2P(Ph$-$Ph)$) and bi-dentate 1,1'-bis(diphenylphosphino)ferrocene (dppf), 1,4-bis(diphenylphosphino)ferrocene (dppb) etc., solvents, such as tetrahydrofuran (THF), dimethoxyethane (DME), dimethylformamide (DMF), 1-methyl-2-pyrrolidinone (NMP) etc., and temperature and bases in the case of the Suzuki reaction such as $K_2CO_3$.

SUMMARY OF THE INVENTION

The present invention relates to processes for making 2,3-disubstituted indoles. More specifically, the invention also provides for a process to make 2,3-disubstituted indoles disclosed in U.S. patent application Ser. No. 10/198,384 and intermediates thereof.

The first embodiment of the invention provides a process for making a compound of general formula I:

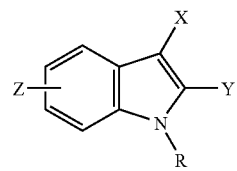

said process comprising reacting a substituted indole compound I':

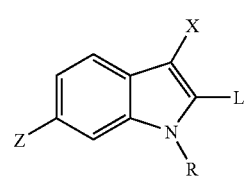

with a heteroaryl or aryl zinc halide:

or di heteroaryl or di aryl zinc:

wherein:
L is Br or Cl
R is H or $C_{1-8}$alkyl
X is $C_3$-$C_8$cycloalkyl, aryl or H, $C_1$-$C_8$alkyl;
Y is heteroaryl or aryl;
Z is H, $HO_2C$—, $C_{1-8}$alkyl $O_2C$—, $C_{1-6}$alkyl HNC(O)—,

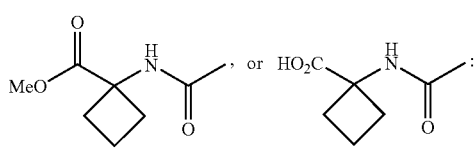

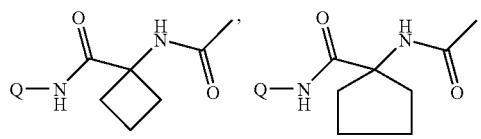
wherein Q is selected from:
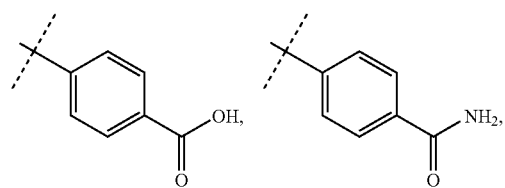
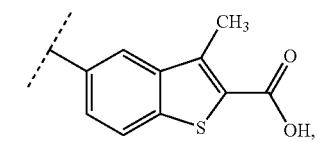
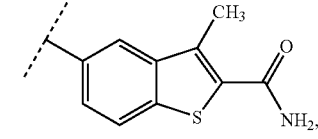
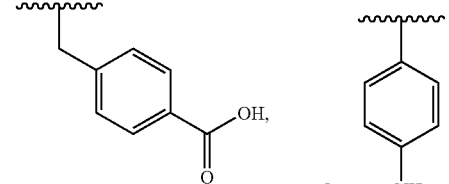
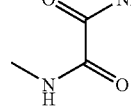
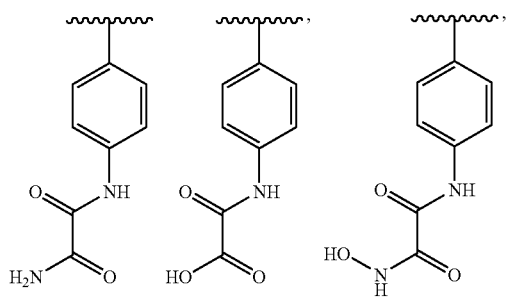
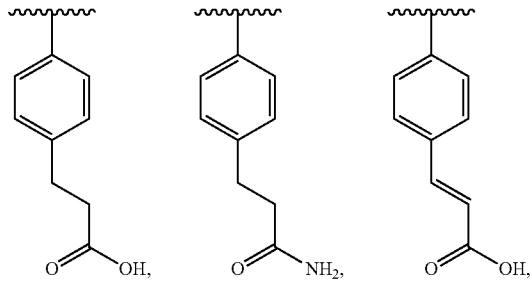
-continued
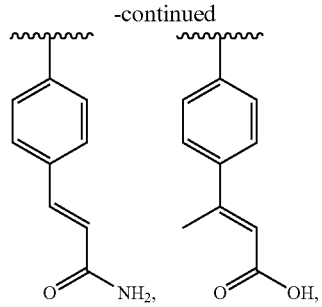
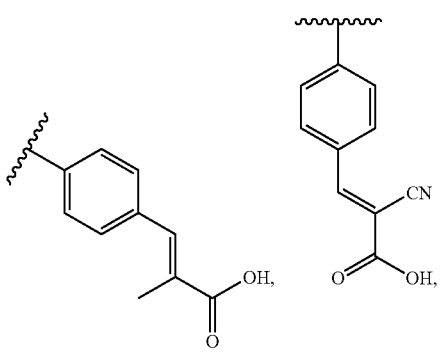
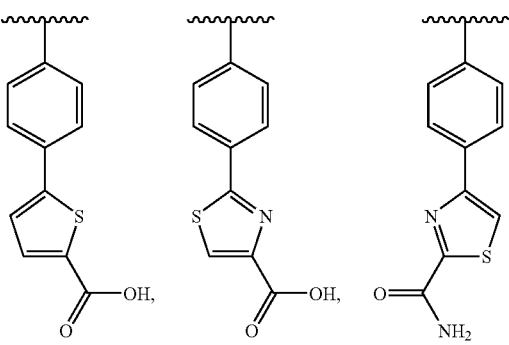
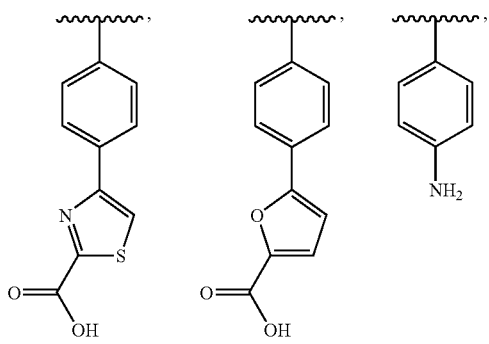

-continued
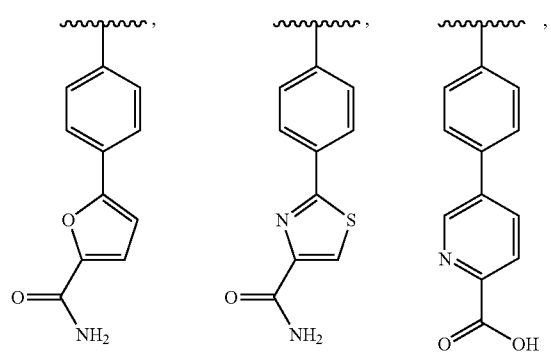
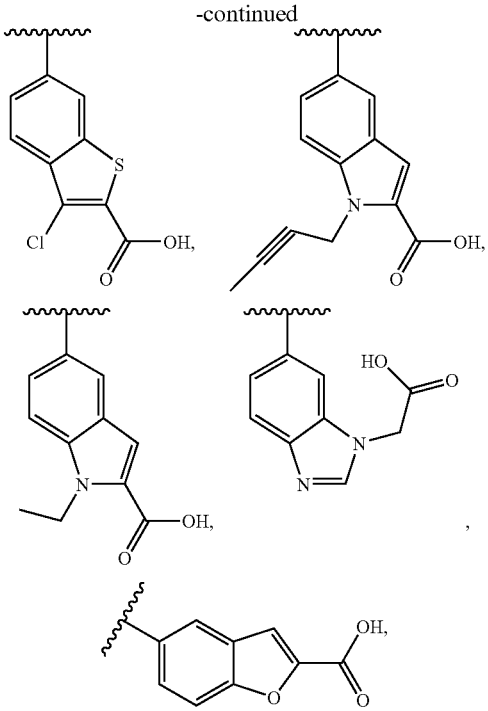
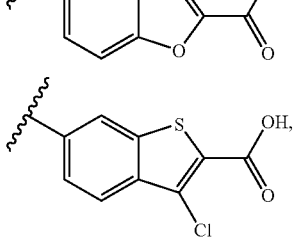
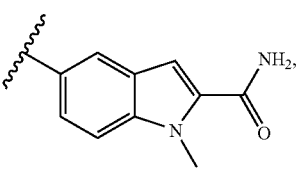
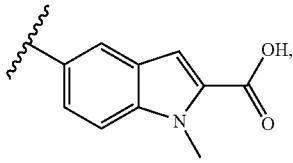
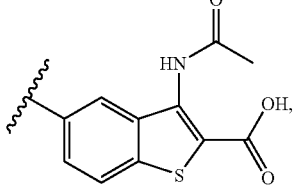
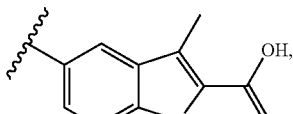
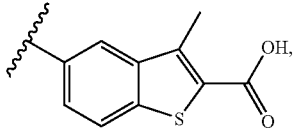

-continued

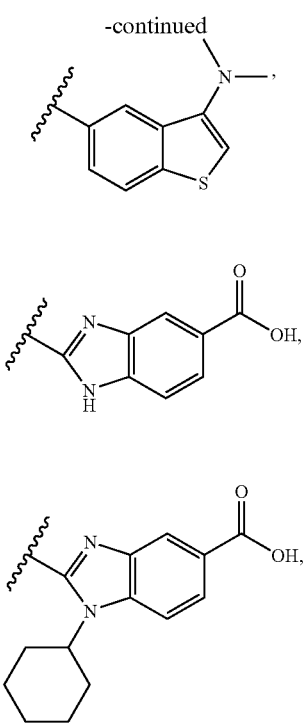

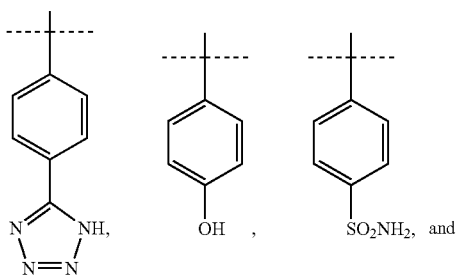

in the presence of a metal catalyst selected from Pd. Ni, a ligand selected from Ph₃P, p-Tol₃P, tri(2-furyl)phosphine, Cy₃P, tBu₃P, Cy₂P(Ph-Ph), dppf and dppb, in a solvent selected from THF, DMF, NMP or a combination thereof, at a temperature of between ambient and 100° C., to provide the desired compound of formula I.

Another aspect of the invention provides the process of the first embodiment wherein the ratio of the desired product is 2.5 fold greater than that that of the 2H indole product.

Another aspect of the invention provides the process of the first embodiment wherein the catalyst is Pd.

Another aspect of the invention provides the process of the first embodiment wherein the ligand is either Ph₃P, Cy₃P or Cy₂P(Ph-Ph).

Another aspect of the invention provides the process of the first embodiment wherein the solvent is a mixture of THF and NMP.

Another aspect of the invention provides the process of the first embodiment for making a compound of formula I as described above wherein L is Br or Cl
R is H or methyl;
X is $C_3$-$C_8$cycloalkyl;
Y is heteroaryl or aryl;
Z is H, $HO_2C-$, $C_{1-8}alkylO_2C-$,

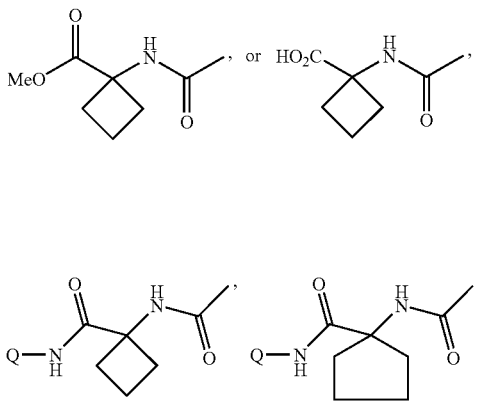

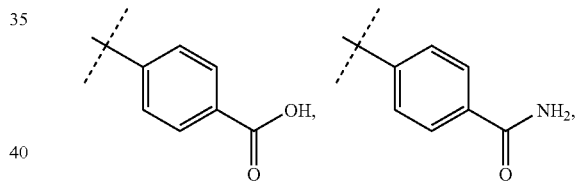

wherein Q is selected from:

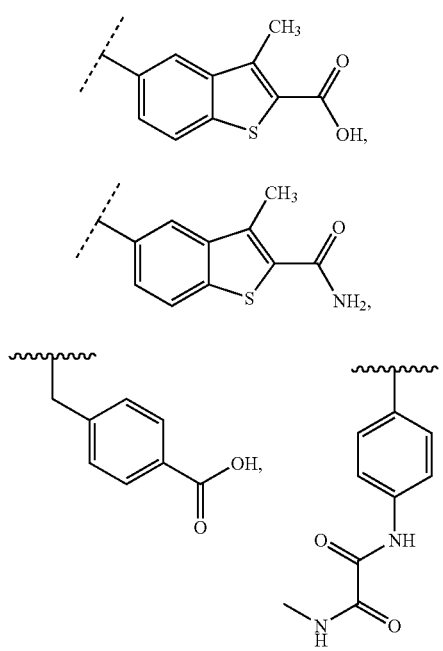

-continued
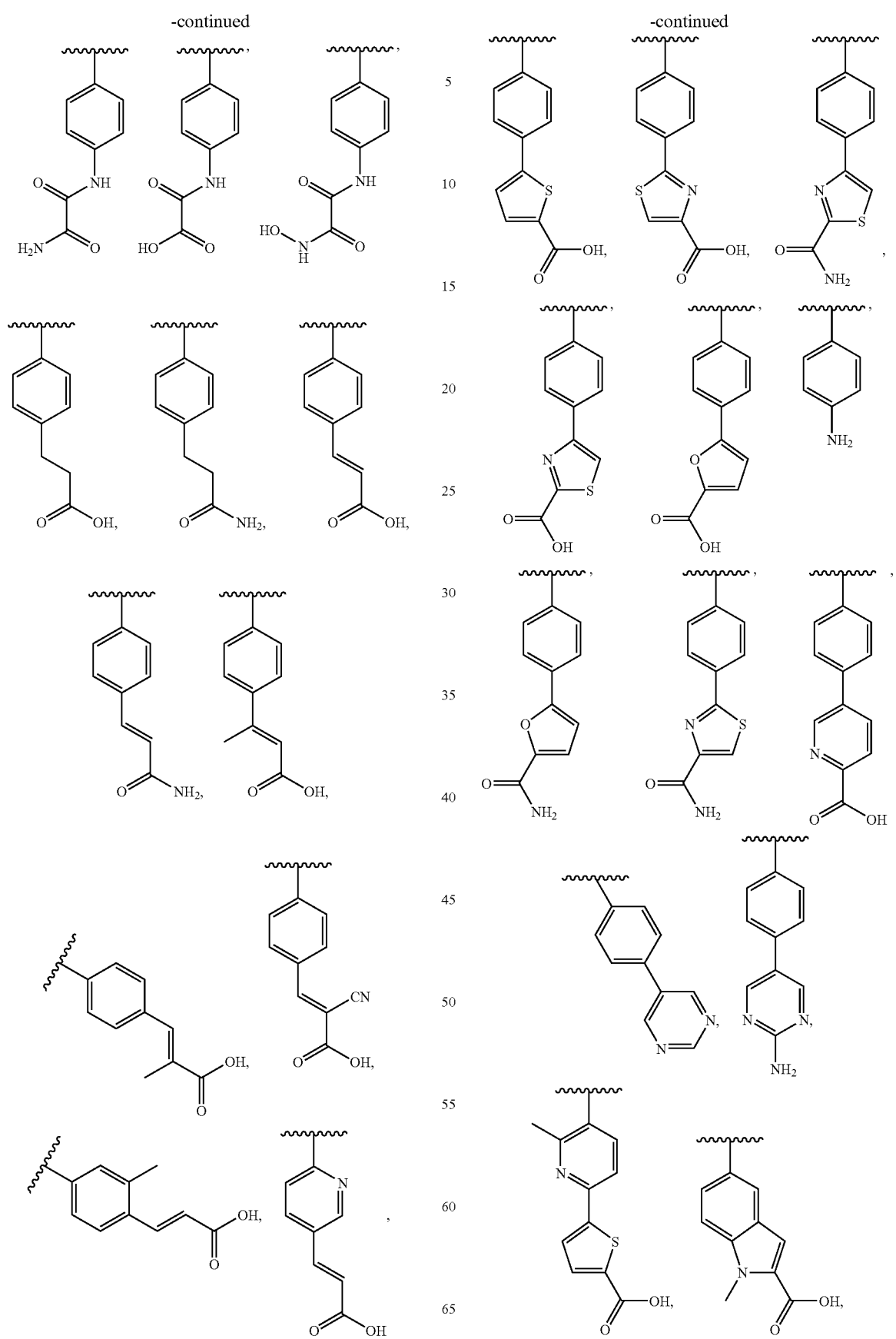

-continued
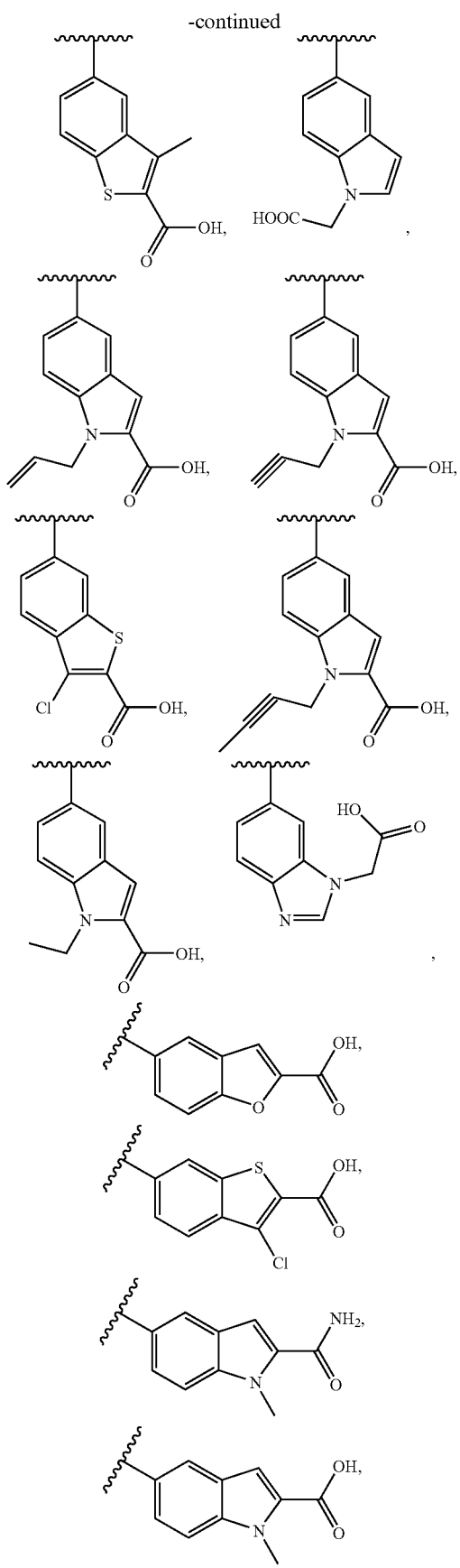
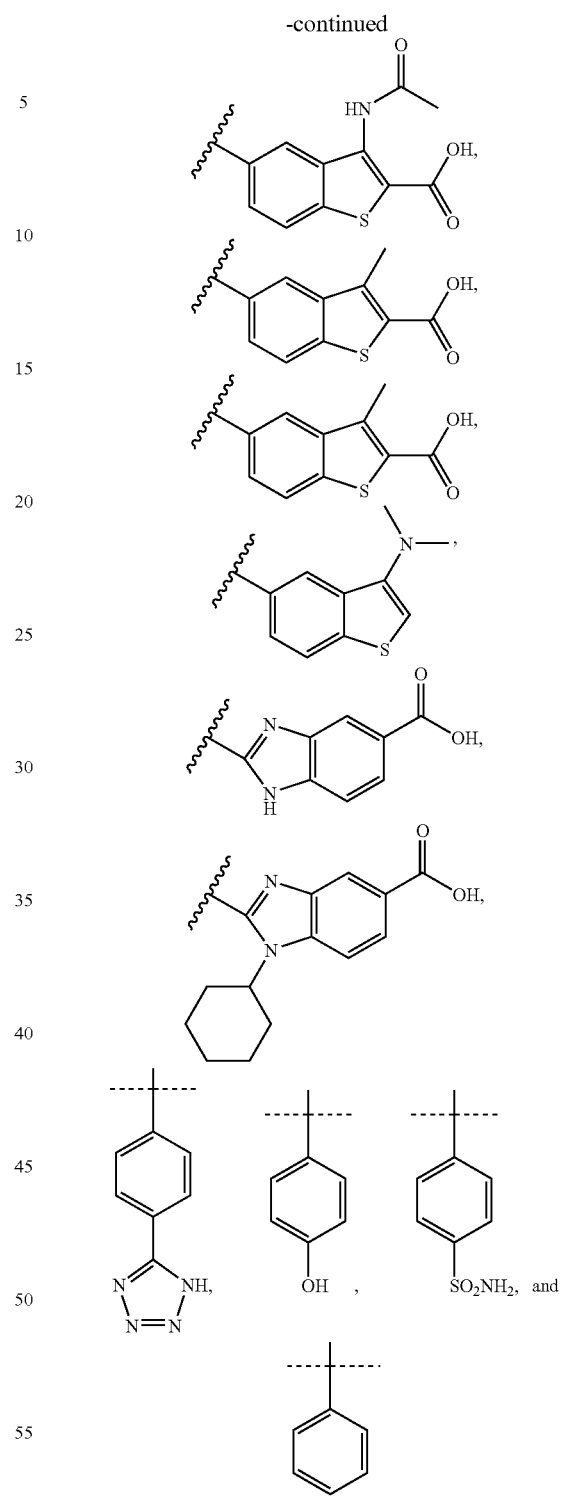
Another aspect of the invention provides the process of the first embodiment for making a compound of formula I:
wherein:
L is Br or Cl
R is H or methyl
X is cyclopentyl
Y is pyridyl
L is Br or Cl; and Z is H, HO$_2$C—, C$_{1-8}$alkylO$_2$C—,
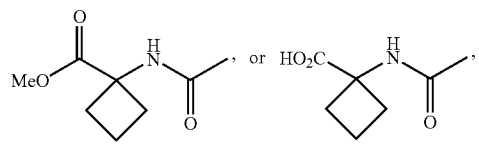
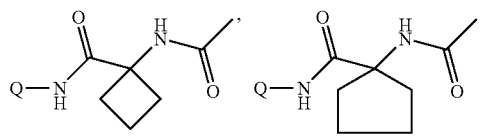
wherein Q is selected from:
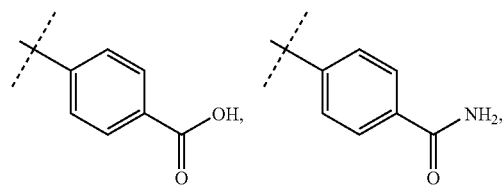
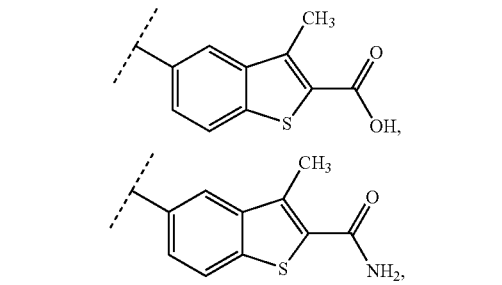
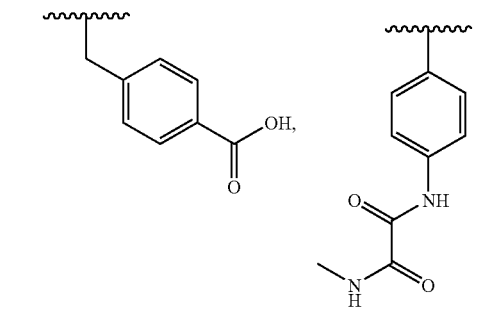
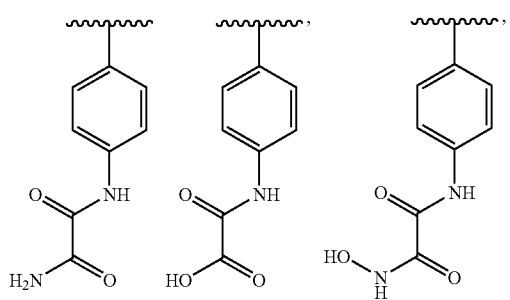
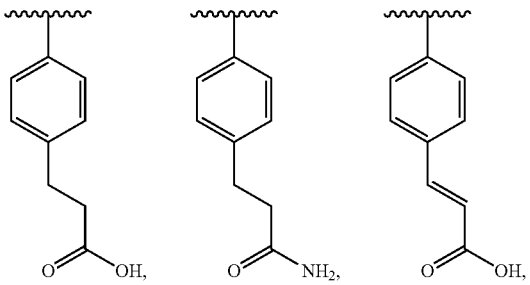
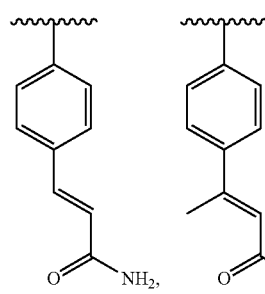
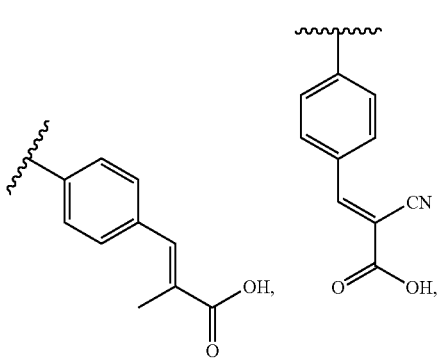
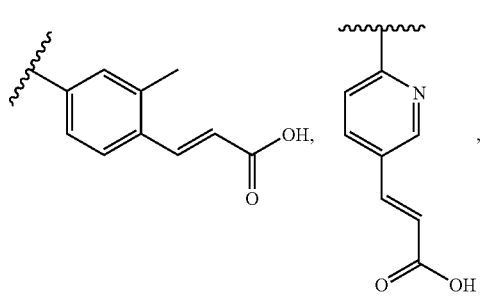
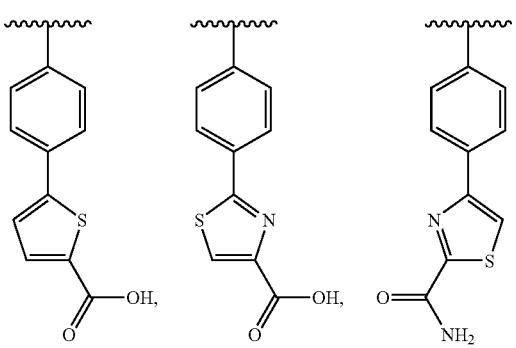

-continued
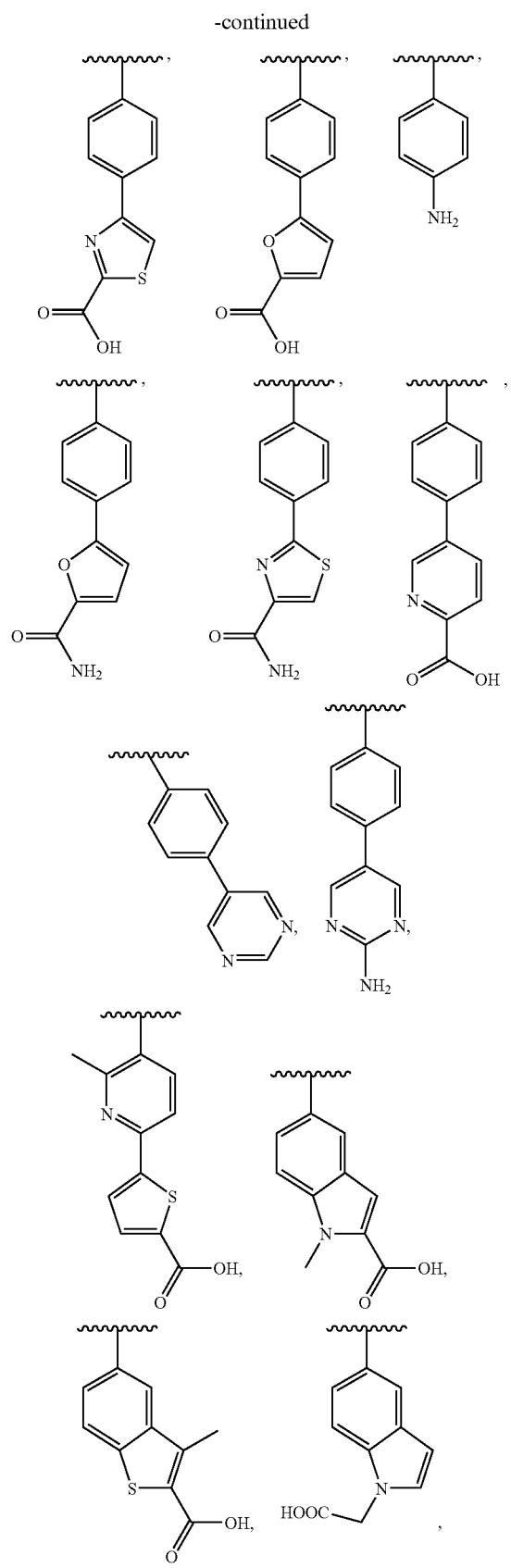
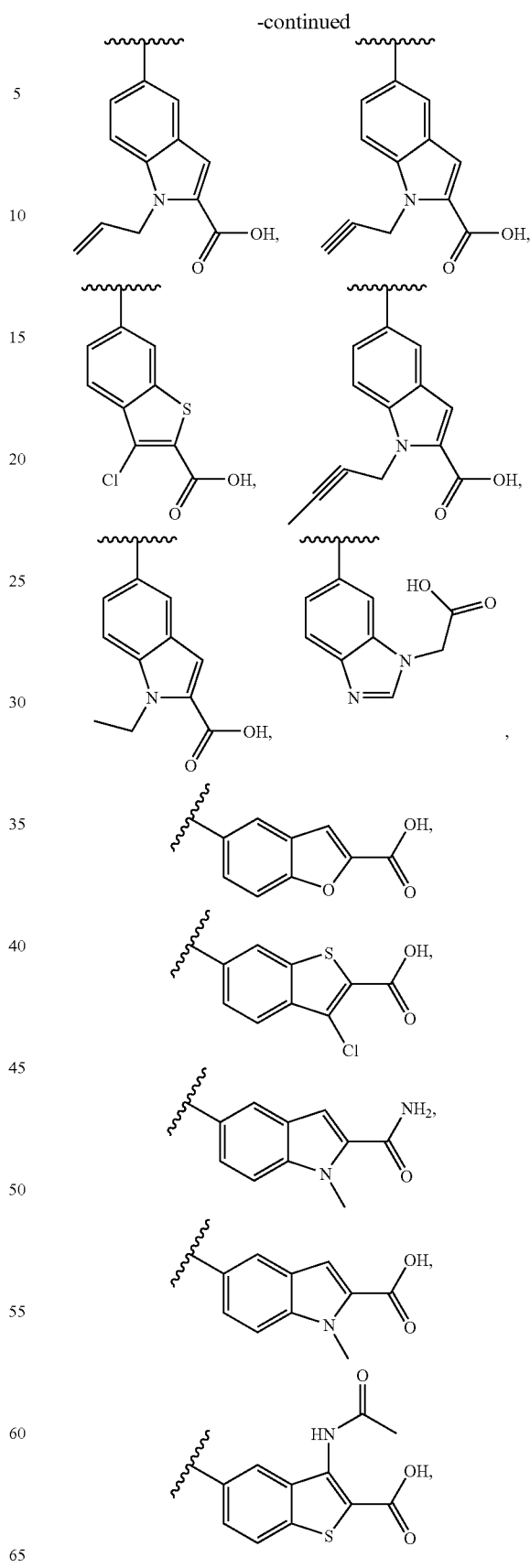

-continued

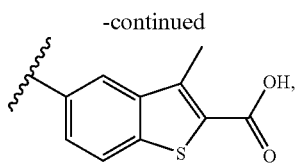

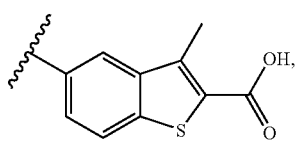

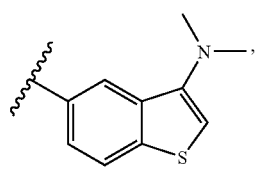

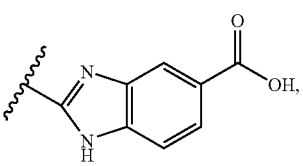

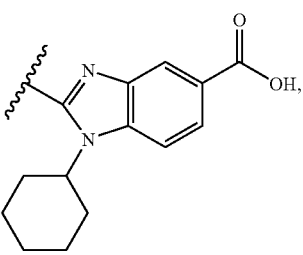

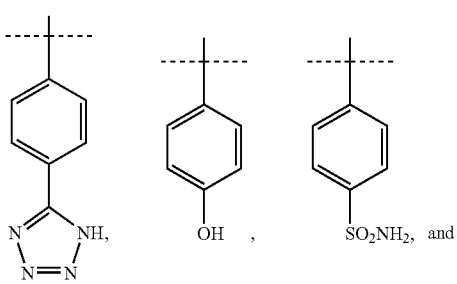

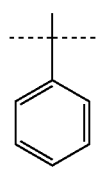

in the presence of Pd(OAc)$_2$ and a ligand selected from Ph$_3$P, (2-furyl)$_3$P, p-Tol$_3$P, dppb and Cy$_3$P in a 2:1 mixture of NMP to THF, at a temperature between 70° C. and 90° C.

Another aspect of the invention provides a process of the first embodiment for making a compound of formula I wherein:

L is Br or Cl
R is H or methyl,
Z is

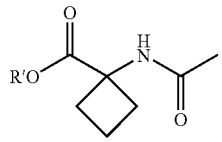

X is cyclopentyl
Y is pyridyl in the presence of Pd(OAc)$_2$ and a ligand selected from Ph$_3$P, (2-furyl)$_3$P, p-Tol$_3$P and Cy$_2$P(Ph-Ph) in a 2:1 mixture of NMP to THF, at a temperature between 70° C. and 90° C.

Another aspect of the invention provides the compound having the formula:

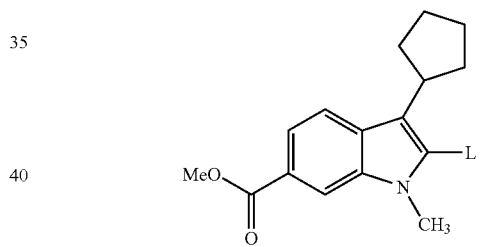

wherein L is Br or Cl.

Another aspect of the invention provides for the compound having the formula:

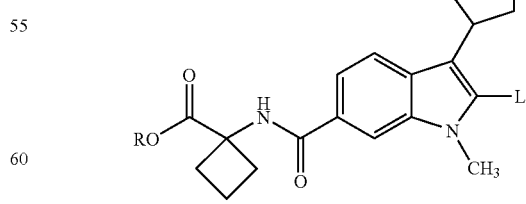

wherein L is Br or Cl; and
R is H or methyl.

DETAILED DESCRIPTION OF THE INVENTION

Terms and Definitions

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

The term "aryl" means a 6-12 membered aromatic carbocycle, which can be a single ring or can be multiple rings fused together or linked covalently. The term "aryl" includes, for example, phenyl and naphthyl; other terms comprising "aryl" will have the same definition for the aryl component, examples of these moieties include: arylalkyl, aryloxy or arylthio.

The term "alkyl" refers to a saturated aliphatic radical containing from one to ten carbon atoms or a mono- or polyunsaturated aliphatic hydrocarbon radical containing from two to twelve carbon atoms unless otherwise stated. The mono- or polyunsaturated aliphatic hydrocarbon radical contains at least one double or triple bond, respectively. "Alkyl" refers to both branched and unbranched alkyl groups. Examples of "alkyl" include alkyl groups which are straight chain alkyl groups containing from one to eight carbon atoms and branched alkyl groups containing from three to ten carbon atoms. Other examples include lower alkyl groups which are straight chain alkyl groups containing from one to six carbon atoms and branched alkyl groups containing from three to six carbon atoms. It should be understood that any combination term using an "alk" or "alkyl" prefix refers to analogs according to the above definition of "alkyl". For example, terms such as "alkoxy", "alkylthio" refer to alkyl groups linked to a second group via an oxygen or sulfur atom. "Alkanoyl" refers to an alkyl group linked to a carbonyl group (C=O). Each alkyl or alkyl analog described herein shall be understood to be optionally partially or fully halogenated.

The term "cycloalkyl" refers to the cyclic analog of an alkyl group, as defined above. Examples of cycloalkyl groups are saturated or unsaturated nonaromatic cycloalkyl groups containing from three to eight carbon atoms, and other examples include cycloalkyl groups having three to six carbon atoms.

The term "heteroaryl" refers to a stable 5-8 membered (but preferably, 5 or 6 membered) monocyclic or 8-11 membered bicyclic aromatic heterocycle radical. Each heterocycle consists of carbon atoms and from 1 to 4 heteroatoms chosen from nitrogen, oxygen and sulfur. The heteroaryl group may be attached by any atom of the ring which results in the creation of a stable structure. Examples of "heteroaryl" include radicals such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl.

The terms "optional" or "optionally" mean that the subsequently described event or circumstances may or may not occur, and that the description includes instances where the event or circumstance occurs and instances in which it does not. For example, "optionally substituted cycloalkyl" means that the cycloalkyl radical may or may not be substituted and that the description includes both substituted cycloalkyl radicals and cyckloalkyl radicals having no substitution.

The term "substituted" means that any one or more hydrogens on an atom of a group or moiety, whether specifically designated or not, is replaced with a selection from the indicated group of substituents, provided that the atom's normal valency is not exceeded and that the substitution results in a stable compound. If a bond to a substituent is shown to cross the bond connecting two atoms in a ring, then such substituent may be bonded to any atom on the ring. When a substituent is listed without indicating the atom via which such substituent is bonded to the rest of the compound, then such substituent may be bonded via any atom in such substituent. Generally, when any substituent or group occurs more than one time in any constituent or compound, its definition on each occurrence is independent of its definition at every other occurrence. Such combinations of substituents and/or variables, however, are permissible only if such combinations result in stable compounds.

In the method of the invention described below a palladium catalyzed cross coupling reaction was applied to the cross coupling of the indole intermediate:

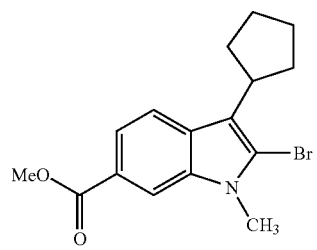

with the commercially available 2-pyridylzinc bromide or the in situ generated di(2-pyridyl)zinc, in the presence of catalyst $Pd(Ph_3P)_4$, generated in situ from $Pd(OAc)_2$ and $Ph_3P$. The results are shown in Table 1.

Starting materials such as those defined by "Z" can be made using the methods taught in U.S. provisional application No. 60/551,107.

Ligands

The selection of ligand was also found to impact the cross coupling reaction of the present invention. Screening of reaction ligands was conducted using the above-mentioned starting materials. The results are shown in Table I. It was found that $Pd(Ph_3P)_4$ or $Pd(PCy_3)_2$ gave good results in terms of the ratio of the desired product compared to an unwanted by-product resulting from dehalogenation rather than coupling (Product/2H-Indole) (See Entries 5, 11, 12).

TABLE I

| No. | Pd | Mol Pd % | Solvent | Temp (° C.) | Time (h) | Conversion (%) | Product/ 2H-Indole[a] |
|---|---|---|---|---|---|---|---|
| 1 | Pd(PPh$_3$)$_4$ | 5 | THF | Reflux | 2 | 46 | 37/63 |
| 2 | Pd(PPh$_3$)$_4$ | 5 | THF | Reflux | 20 | 100 | 52/48 |
| 3 | Pd(PPh$_3$)$_4$ | 2 | THF | Reflux | 2 | — | 52/48[b] |
| 4 | Pd(PPh$_3$)$_4$ | 5 | THF | Reflux | 5 | 53 | 52/48[c] |
| 5 | Pd(PPh$_3$)$_4$ | 5 | THF-NMP | RT | 20 | 24 | 74/26 |
| 6 | Pd(PPh$_3$)$_4$ | 5 | THF-NMP | Reflux | 4 | ~100 | 74/26 |
| 7 | POPd[d] | 10 | THF-NMP | Reflux | 1 | 100 | 24/76 |
| 8 | POPd | 5 | THF-NMP | Reflux | 2 | 100 | 37/63 |
| 9 | POPd | 5 | THF-NMP | RT | 20 | 45 | 10/90 |
| 10 | POPd | 5 | THF-NMP | Reflux | 2 | 100 | 33/67 |
| 11 | PXPd[e] | 5 | THF-NMP | Reflux | 4 | 68 | 45/55 |
| 12 | Pd(PCy$_3$)$_2$ | 5 | THF-NMP | RT | 20 | 45 | 82/18 |
| 13 | Pd(PCy$_3$)$_2$ | 5 | THF-NMP | Reflux | 2 | 85 | 78/22 |
| 14 | Pd(PCy$_3$)$_2$ | 5 | THF-NMP | 40 | 20 | 67 | 76/24 |
| 15 | Pd(PCy$_3$)$_2$ | 5 | THF-NMP | 40 | 96 | 92 | 75/25 |
| 16 | Pd(PCy$_3$)$_2$ | 5 | THF-NMP | RT | 96 | 59 | 82/18 |
| 17 | Pd(P(tBu$_3$)$_2$ | 5 | THF-NMP | 40 | 20 | 32 | 30/70 |
| 18 | Pd(P$^t$Bu$_3$)$_2$ | 5 | THF-NMP | RT | 96 | 26 | 38/62 |
| 19 | PdCl$_2$(dppf) | 5 | THF-NMP | " | 20 | 40 | 65/35 |
| 20 | Pd$_2$(dba)$_3$/PCy$_3$ (1:2) | 5 | THF-NMP | " | 3 | 60 | 59/41 |
| 21 | Pd$_2$(dba)$_3$/PCy$_3$ (1:4) | 5 | THF-NMP | " | 3 | 51 | 67/33 |
| 22 | Pd$_2$(dba)$_3$/PCy$_3$ (1:6) | 5 | THF-NMP | " | 3 | 55 | 68/32 |
| 23 | Pd$_2$(dba)$_3$/L (1:4)[f] | 5 | THF-NMP | " | 20 | 54 | 27/73 |

[a]All reactions were run using 2 equivalents of 2-PyZnBr under argon and the ratio of product and by-product 2H-indole was determined based on the HPLC integration.
[b]Indole-zinc reagent and 2-PyBr were used.
[c]The starting material was pre-treated over MgSO$_4$ in CH$_2$Cl$_2$.
[d]POPd is PdCl$_2$[(t-Bu]$_2$P(OH)]$_2$.
[e]PXPd is PdCl$_2$[(t-Bu]$_2$PCl]$_2$.
f) L is 1,3-bis(adamantyl)imidazol-2-ylidene, a carbene ligand Solvents One of the major considerations in achieving an optimized reaction for the above palladium catalyzed cross coupling reaction is minimizing the formation of the 2H-indole by product. It has been found that the ratio of the desired product vs. the 2H-indole by-product was impacted by the selection of solvent(s). As shown in Table I when THF was used as the sole solvent in the process, the ratio of the desired product vs. the by-product was 52:48 (entries 1-3). Whereas when the NMP-THF (2:1) solvent combination was used as the solvent this ratio was improved. A ratio of 1.5:1 is preferred. Optimum conditions shown in Scheme II provided a ratio of 94:6.

Scheme II

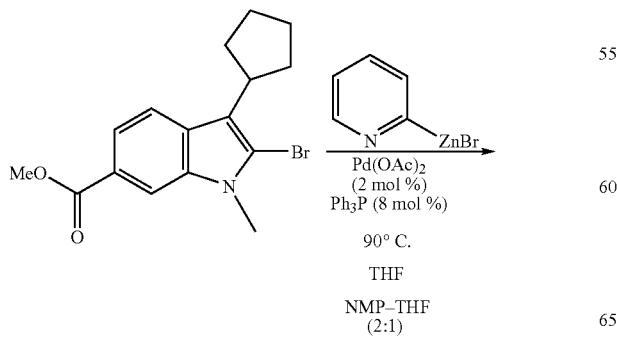

-continued

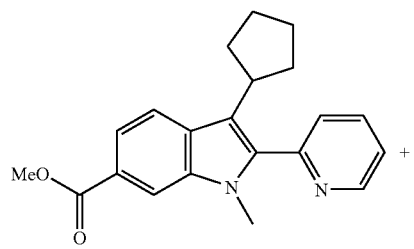

52%
94%

+

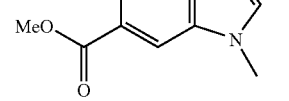

By-product

48%
6%

The preferred solvents are DMSO, DMF, DMAC, DMA, NMP, N-ethyl pyrrolidinone, 1,3-dimethyl-2-imidazolidinone. The most preferred solvent is NMP. The preferred combination of solvents is NMP-THF (2:1).

Temperature

The temperature was also found to impact the cross coupling reaction of the present invention. For example the reaction took over 24 hours to complete at 70° C., while it only took 3 hours at 90° C. The preferred temperature is between 70 and 90° C.

The present invention discloses a method that can be used for the production of cross coupled indole compounds on a large scale (25 kg), by coupling of a 2-bromoindole with an aryl or heteroaryl zinc species intermediate. One embodiment of the invention provides a method for making tri-substituted indoles such as 3-cyclopentyl-6-methoxycarbonyl-2-(2-pyridyl)indole by coupling of 1-methyl-2-bromo-3-cyclopentyl-6-methoxycarbonyl indole with either 2-pyridylzinc bromide or di(2-pyridyl)zinc (Scheme II).

Use of Aryl Chlorides

In another aspect of the present invention it has been found that the 2-chloro indole intermediate can be used in a palladium catalyzed cross coupling of aryl chlorides as shown in Scheme III. The cost for aryl chlorides is often significantly lower than the corresponding bromo or iodo analog. Considering the ready availability of the 2-chloro indole starting material, this present invention provides an economical route to generate a variety of 2,3-disubstituted indole compounds with important medicinal value.

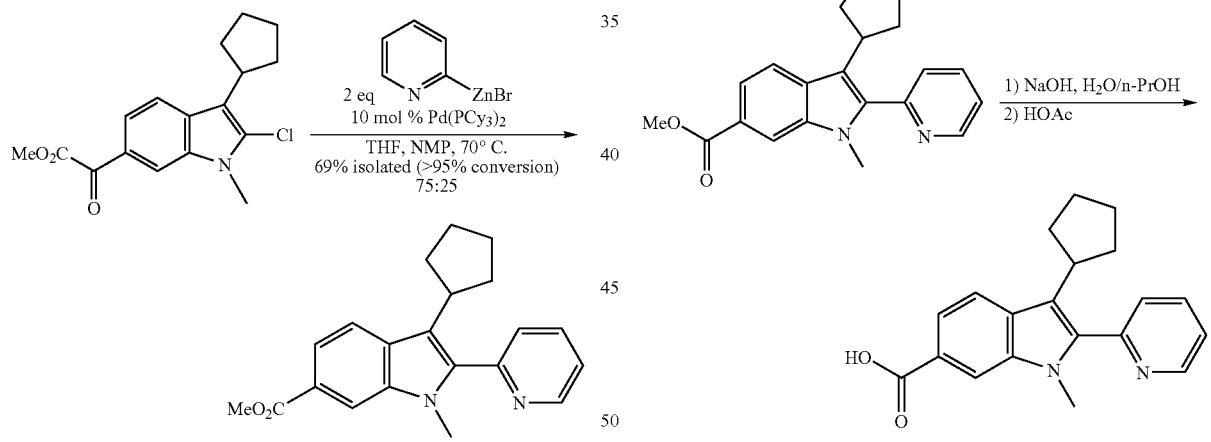

Results for the above reaction under various other conditions are illustrated in Table II below.

TABLE II

| Catalyst | Conditions | Product/2-H Indole | Isolated Yield |
|---|---|---|---|
| 5 mol % Pd(PCy$_3$)$_2$ | 8 Vol NMP, 16 Vol THF, 66° C., 7 h | ~75:25 | 46% |
| 7.5 mol % Pd(OAc)$_2$, 25 mol % PCy$_3$, (2 portions) | 8 Vol NMP, 16 Vol THF, 66° C., 24 h | 75:25 | 56% |
| 10 mol % Pd(OAc)$_2$, 40 mol % PCy$_3$, | 8 Vol NMP, 16 Vol THF, 66° C., 26 h | 75:25 | 69% |
| 6 mol % Pd(OAc)$_2$, | 8 Vol NMP, 16 Vol | 83:17 | 72% |

TABLE II-continued

| Catalyst | Conditions | Product/2-H Indole | Isolated Yield |
|---|---|---|---|
| 24 mol % PCy$_3$, (2 portions) | THF, 66° C., 30 h (90% Conversion) | | (HCl salt) |
| 10 mol % Pd(OAc)$_2$, 40 mol % PCy$_3$, | 8 Vol NMP, 16 Vol THF, 66° C., 24 h | 80:20 | 62% |

SYNTHETIC EXAMPLES

Example 1

Preparation of 3-cyclopentyl-1-methyl-2-(pyridine-2-yl)-1H-indole-6-carboxylic acid

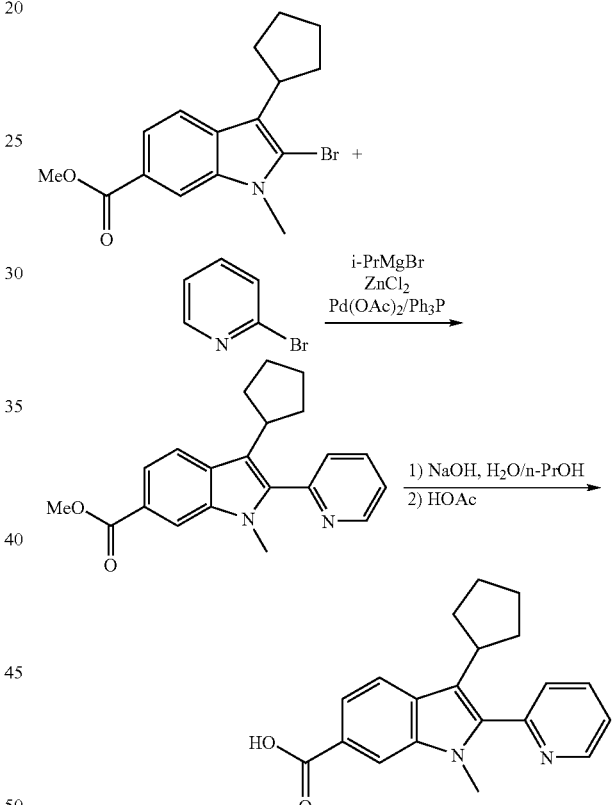

1448 g (2.97 mol, 2.0 eq) of isopropylmagnesium chloride (2 M in THF) was charged to a dried reactor under nitrogen. 474 g (3.0 mol, 2.02 eq) of 2-bromopyridine was charged to the reactor over 1 h, while maintaining the content temperature at 35-45° C. The mixture was stirred at 40° C. for over 1 h. After cooling to 35-40° C., the reaction mixture was charged with 368 g (1.634 mol, 1.1 eq) of ZnBr$_2$ while maintaining the temperature below 65° C. After addition, the mixture was warmed to 65° C. for 1 h. After cooling to 35-40° C., the reaction mixture was charged with 3046 g of NMP, followed by addition of 202.4 g (1.487 mol, 1.0) of methyl benzoate. The reaction mixture was warmed to 65° C. for another 1 h, then cooled to 35° C. To the mixture was added sequentially 6.66 g (0.029 mol, 0.02 eq) of palladium acetate, 31.14 g (0.119 mol, 0.08 eq) of PPh$_3$ and 500.0 g (1.487 mol, 1.0 eq) of 2-bromo-3-cyclopentyl-1-methyl-1H- indole-carboxylic acid methyl ester. After addition, the reaction mixture was warmed to 70° C. over 1 h, then warmed to 90° C. and stirred at 90° C. for 3 h. After completion, 25.2 g (0.124 mol, 0.083 eq) of tributyl phosphine, 2600 g of isopropyl acetate, and 3270 g of saturated ammonium solution were added sequentially to the reaction mixture. After agitating for 1 h, the batch contents were filtered and the solid was washed with 2×670 g of isopropyl acetate. The organic phase was separated, washed with 2×2230 g of 10% aq. NH$_4$Cl, and then treated with 1484 ml of 4 M aq. HCl. The lower aq. phase was separated and the organic layer was extracted two times with 744 ml of 4 M aq. HCl. The aqueous phases were combined followed by the addition then 602 g of 1-propanol and 0.2176 g (16.32 mol, 11.0 eq) of 50% sodium hydroxide were added. The resultant mixture was heated to 89° C. for 2 h until the hydrolysis reaction was completed. The mixture was cooled to 25° C. and filtered through 0.5 micron in-line filter. To the filtrate was added 322 g (5.36 mol, 3.6 eq) of acetic acid. After warming at 60° C. for 1 h, the mixture was cooled to 25° C. over 2 h. The solid was filtered and the wet cake was washed with 2×1000 ml of a 1:2 mixture of 1-propanol and water, followed with 2×500 g of water. 365 g of the title compound was obtained after drying at 40° C. under vacuum with nitrogen purge (77% yeild).

Example 2

Preparation of 1-[(3-cyclopentyl-1-methyl-2-(pyridin-2-yl)-1H-indole-6-carbonyl)-amino]-cyclobutanecarboxylic acid

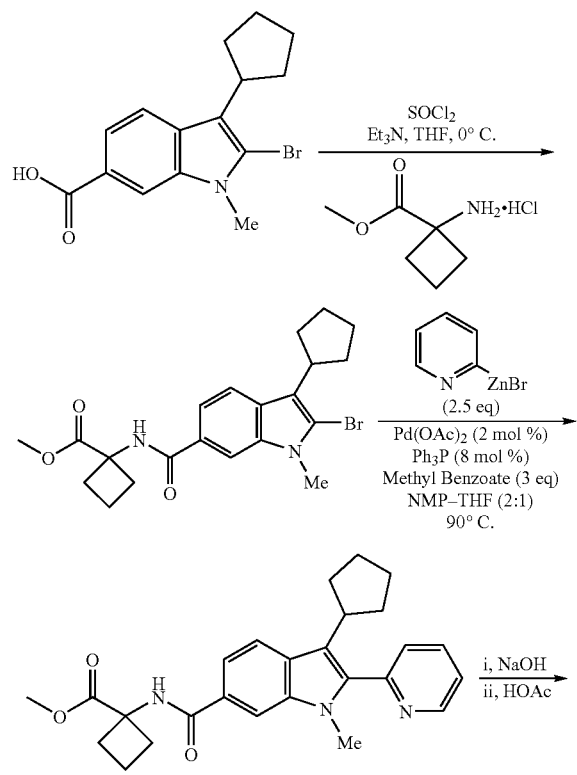

-continued

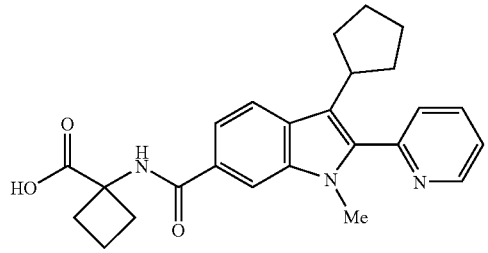

2-Bromo-3-cyclopentyl-1-methyl-1H-indole-6-carboxylic acid (32.22 g, 100.0 mmol) was suspended in anhydrous THF (322 mL). Triethylamine (62.72 mL, 450.0 mmol) was added. The solution was cooled to 5° C. in an ice-water bath. Thionyl chloride (8.73 mL, 120.0 mmol) was slowly added under vigorous stirring. After addition, the suspension was stirred at 5° C. for 1 h and then at room temperature overnight. HPLC indicated 74% conversion of the starting material (quenched with diethylamine). Additional triethylamine (32.06 mL, 230.0 mmol) was added under stirring followed by slow addition of thionyl chloride (3.64 mL, 50.0 mmol). The mixture was stirred at room temperature (@25° C.) for 4 h. The conversion of the starting material remained almost unchanged as shown by HPLC. 1-Methoxycarbonyl-cyclobutyl-ammonium chloride (17.39 g, 105.0 mmol) was added and the mixture was stirred at room temperature for 4 h. HPLC indicated that 77% coupling product was formed while 22% of starting material remained. Acetic acid (74.42 mL, 1300 mmol) and water (322 mL) were added to obtain a brownish solution (pH~6). THF (~250 mL) was distilled at normal pressure. The precipitate was collected by filtration, washed with 1/1 acetonitrile/water (2×150 mL) and water (150 mL), and dried to give a solid (37.00 g). The crude product was suspended in ethyl acetate (450 mL) and the mixture was heated to reflux for 0.5 h. The mixture was allowed to cool to room temperature. The solid was collected by filtration, washed with ethyl acetate (3×50 mL) and dried to give 1-[(2-bromo-3-cyclopentyl-1-methyl-1H-indole-6-carbonyl)-amino]-cyclobutanecarbox acid methyl ester (17.26 g, 40%). The filtrate was concentrated to dryness on vacuum. The residual solid was dissolved in THF (50 mL). The solution was passed through a short column of neutral aluminum oxide (activated, Brockmann I, 150 g) and eluted with THF (300 mL). Removal of solvent provided a second crop of product (11.20 g, 26%). The yield of the combined product based on the converted starting material was ~86%. $^1$H NMR (400 MHz, DMSO-d$_6$) δ 9.02 (s, 1H), 8.09 (s, 1H), 7.61 (br s, 2H), 3.80 (s, 3H), 3.62 (s, 3H), 3.30-3.26 (m, 1H), 2.62-2.57(m, 2H), 2.38-2.30(m, 2H), 2.05-1.91 (m, 8H), 1.81-1.62 (m, 2H).

To a solution of i-PrMgCl in THF (10 mL, 20 mmol) was added 2-bromopyridine (1.93 g, 20.2 mmol) at room temperature in one portion. The mixture was stirred at 35° C. for 0.5 h. To the deep-red solution was added ZnBr$_2$ (4.50 g, 20 mmol) under argon and the resulting mixture was stirred at 70° C. for 0.5 h to obtain a thick off-white slurry. 1-Methyl-2-pyrrolidinone (20 mL) was added and followed by methyl benzoate (1.1 mL, 8.7 mmol). The mixture was stirred at 70° C. for 0.5 h and then cooled to room temperature. Palladium acetate (39.1 mg, 0.17 mmol), triphenylphosphine (182.6 mg, 0.70 mmol) and 1-[(2-bromo-3-cyclopentyl-1-methyl-1H-indole-6-carbonyl)-amino]-cyclobutanecarboxylic acid methyl ester (3.768 g, 8.70 mmol) were added. The mixture was stirred at 90° C. until no starting material was left (~3 h) as monitored by HPLC. Saturated ammonium chloride (20 mL), isopropyl acetate (20 mL) and THF (10 mL) were added. The pH of the mixture was adjusted to 4-5 using 4 HCl (~3 mL) and the mixture was stirred at 60° C. for 5 minutes and then transferred to a separatory funnel. The aqueous layer was separated and extracted with isopropyl acetate (20 mL) at 60° C. The combined organic phases were washed with a mixture of saturated ammonium chloride (10 mL) and water (10 mL) at 60° C. The organic layer was extracted with 4 N HCl (15 and 10 mL). To the combined extracts cooled in an ice-water bath was slowly added 50% NaOH (9.40 g, 117.5 mmol). The mixture was heated to reflux until the batch inside temperature reached 89-90° C. n-Propanol (10 mL) was added and the mixture was stirred at 90° C. for 1 h. After the mixture was cooled to 60° C., acetic acid (1.57 g, 26.1 mmol) was slowly added to adjust the pH to 5-6. The resulting white suspension was stirred at 60° C. for 1 h and allowed to cool to room temperature in 2 h. The white precipitate was collected by filtration and the wet cake was rinsed with 2:1 water/n-propanol (15 mL) and water (50 mL). The solid was dried under vacuum until a constant weight (2.67 g, 74%). $^1$H NMR (400 MHz, DMSO-$d_6$) δ 12.25 (s, 1H), 8.92 (s, 1H), 8.80 (d, J=4.0 Hz, 1H), 8.13 (s, 1H), 7.98 (dt, J=1.5, 7.5 Hz, 1H), 7.70 (d, J=8.5, 1H), 7.68-7.56 (m, 2H), 7.52-7.45 (m, 1H), 3.71 (s, 3H), 3.21-3.08 (m, 1H), 2.68-2.55 2H), 2.42-2.28 (m, 2H), 2.05-1.80 (m, 8H), 1.70-1.55 (m, 2H).

Example 3

Preparation of 1-[(3-cyclopentyl-1-methyl-2-pyridin-2-yl-1H-indole-6-carbonyl)-amino]-cyclobutanecarboxylic acid

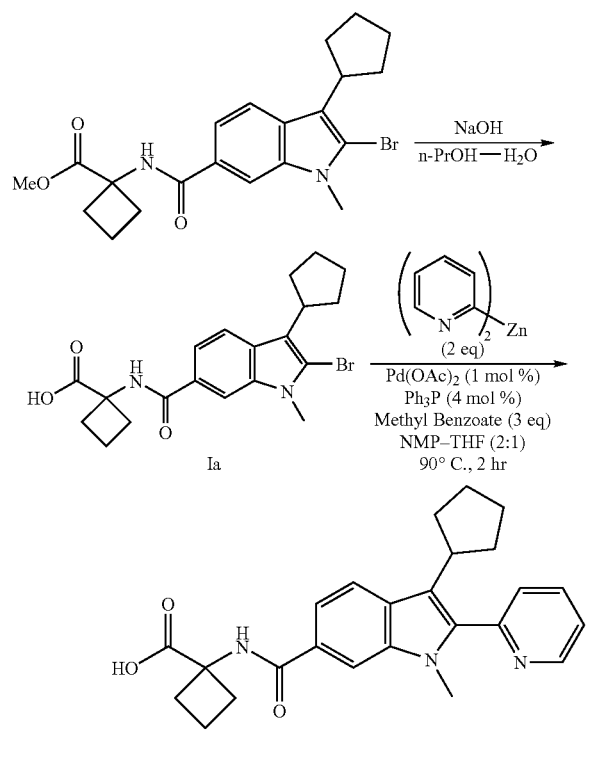

To a suspension of 1-[(2-bromo-3-cyclopentyl-1-methyl-1H-indole-6-carbonyl)-amino]-cyclobutanecarboxylic acid methyl ester (20.00 g, 46.15 mmol) in n-propanol (100 mL) and water (100 mL) was added 50% NaOH (4.06 g, 50.77 mmol). The mixture was heated at 89° C. until no starting material was left (0.5 h). The clear solution was cooled to 50° C. and acetic acid (4.23 mL, 73.85 mmol) was added dropwise to adjust the pH to 5-6. The product was precipitated as a white solid. The suspension was brought to reflux for 0.5 h and then allowed to cool to room temperature in no less than 1 h. The solid was collected by filtration, washed by 1:1 water/n-propanol (100 mL) and water (200 mL). The 1-[(2-bromo-3-cyclopentyl-1-methyl-1H-indole-6-carbonyl)-amino}-cyclobutanecarboxylic acid, obtained as a white solid was dried under vacuum until constant weight (17.78 g, 97%).

To a solution of i-PrMgCl in THF (10 mL, 20 mmol) was added 2-bromopyridine (1.93 g, 20.2 mmol) at room temperature in one portion. The mixture was stirred at 35° C. for 0.5 h. To the deep-red solution was added ZnBr$_2$ (2.477 g, 11 mmol) under argon and the resulting mixture was stirred at 70° C. for 0.5 h to brown-red solution. 1-Methyl-2-pyrrolidinone (20 mL) was added and the mixture was stirred at 70° C. for 10 minutes. Palladium acetate (11.2 mg, 0.05 mmol), triphenylphosphine (52.5 mg, 0.20 mmol) and 1-[(2-bromo-3-cyclopentyl-1-methyl-1H-indole-6-carbonyl)-amino]-cyclobutanecarboxylic acid (2.097 g, 5 mmol) were added. The mixture was stirred at 90° C. for 6 h. Saturated ammonium chloride (20 mL) and THF (20 mL) were added. The pH of the mixture was adjusted to 4-5 using 4 HCl (~3 mL) and the mixture was stirred at 60° C. for 5 minutes. The aqueous layer was separated and extracted with isopropyl acetate (20 mL) at 60° C. The combined organic phases were combined and washed with a mixture of saturated ammonium chloride (10 mL) and water (10 mL) at 60° C. The organic layer was extracted with 4 N HCl (10 and 5 mL). To the combined extracts cooled in an ice-water bath was slowly added 50% NaOH (5.60 g, 70 mmol). The mixture was heated to reflux until the internal temperature reached 89-90° C. The mixture was cooled to 60° C. and n-propanol (10 mL) was added. While stirring, acetic acid (1.14 mL, 20 mmol) was added to adjust the pH to 5-6. The resulting white suspension was stirred at 60° C. for 1 h and allowed to cool to room temperature (@200° C.). The white precipitate was collected by filtration and the wet cake was rinsed with 2:1 water/n-propanol (15 mL) and water (50 mL). The solid was dried under vacuum to provide the title compound (1.65 g, 79%).

Example 4

Preparation of 1-[(3-cyclopentyl-1-methyl-2-pyridin-2-yl-1H-indole-6-carbonyl)-amino]-cyclobutanecarboxylic acid methyl ester

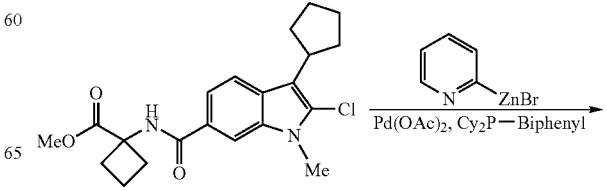

-continued

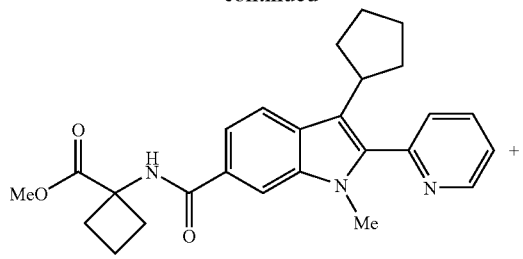

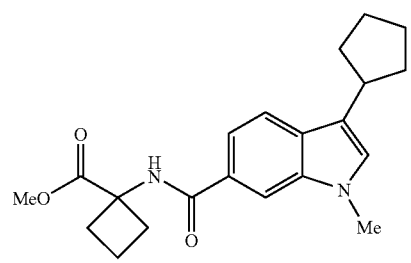

To a solution of i-PrMgCl in THF (10 mL, 20 mmol) was added 2-bromopyridine (1.93 g, 20.2 mmol) at room temperature in one portion. The mixture was stirred at 35° C. for 0.5 h. To the deep-red solution was added ZnBr$_2$ (4.50 g, 20 mmol) under argon and the resulting mixture was stirred at 70° C. for 0.5 h to obtain a thick white slurry. 1-Methyl-2-pyrrolidinone (20 mL) was added and followed by methyl benzoate (2.5 mL, 20 mmol). The mixture was stirred at 70° C. for 0.5 h. The mixture was cooled to room temperature. Palladium acetate (56.1 mg, 0.25 mmol), 2-dicyclohexylphosphinobiphenyl (350.5 mg, 1 mmol) and 1-[(2-chloro-3-cyclopentyl-1-methyl-1H-indole-6-carbonyl)-amino]-cyclobutanecarboxylic acid methyl ester (1.944 g, 5 mmol) were added. The mixture was stirred at 90° C. until no starting material was left (~4 h) as monitored by HPLC. The ratio of the coupling product and the starting material was estimated to be 78/22 by HPLC.

The invention claimed is:

1. A process for making a compound of formula I:

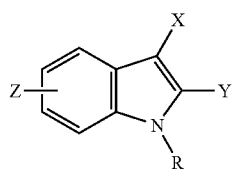

I said process comprising reacting a substituted indole compound I':

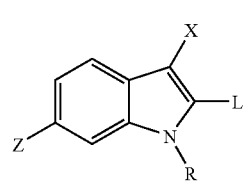

I' with a heteroaryl or aryl zinc halide of the following formula:

or a di heteroaryl or di aryl zinc compound of the following formula:

wherein:
L is Br or Cl
R is H or $C_{1-8}$ alkyl
X is $C_3$-$C_8$ cycloalkyl, aryl, $C_1$-$C_8$ alkyl;
Y is heteroaryl or aryl;
Z is H, HO$_2$C—, $C_{1-8}$ alkyl O$_2$C—, $C_{1-6}$ alkyl HNC(O)—,

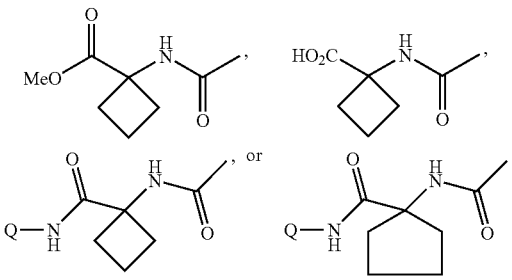

wherein Q is selected from:

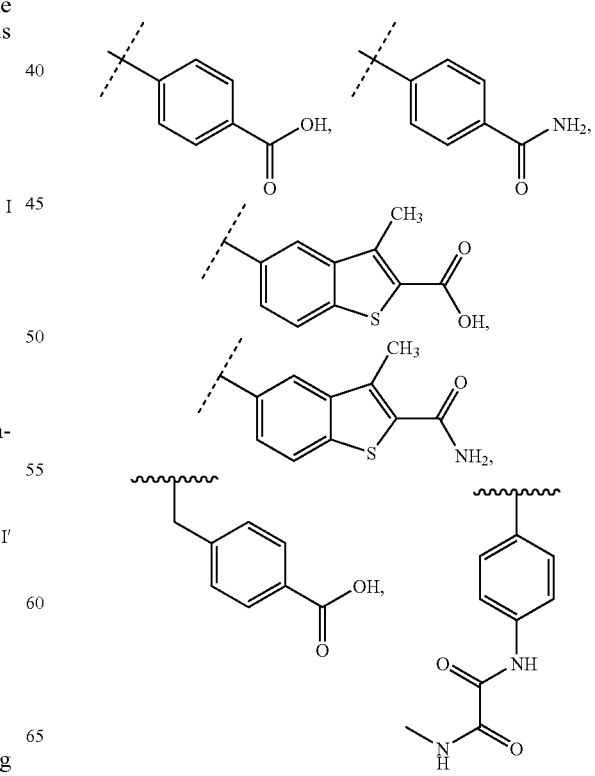

-continued
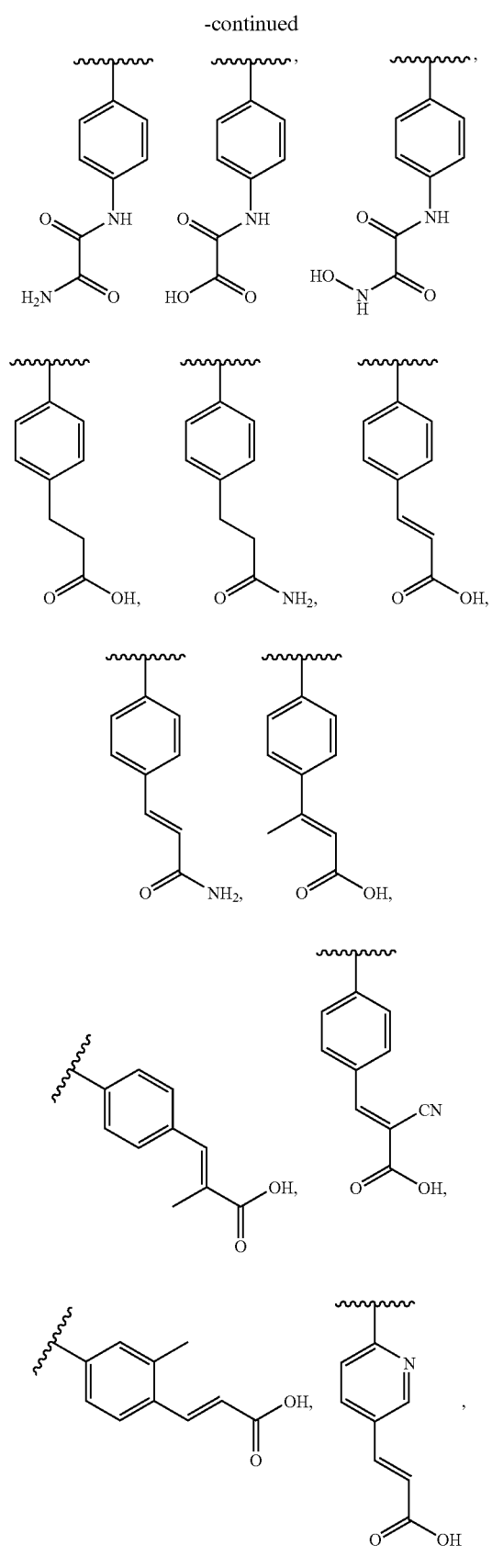
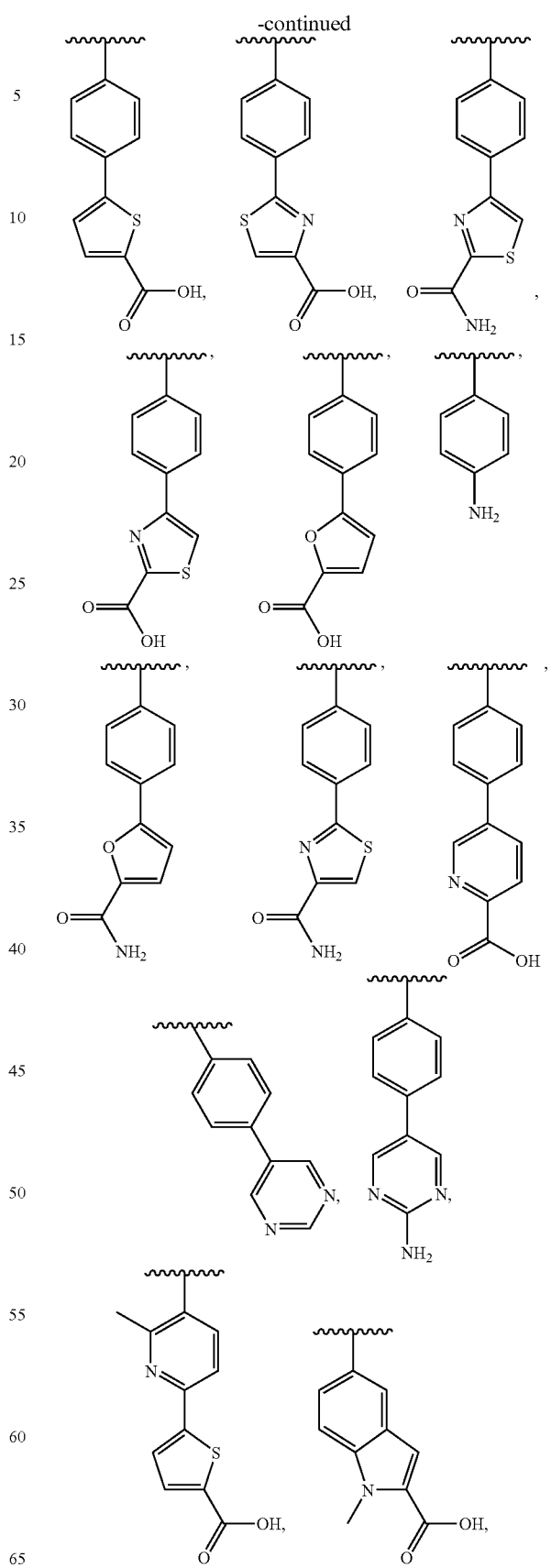

-continued
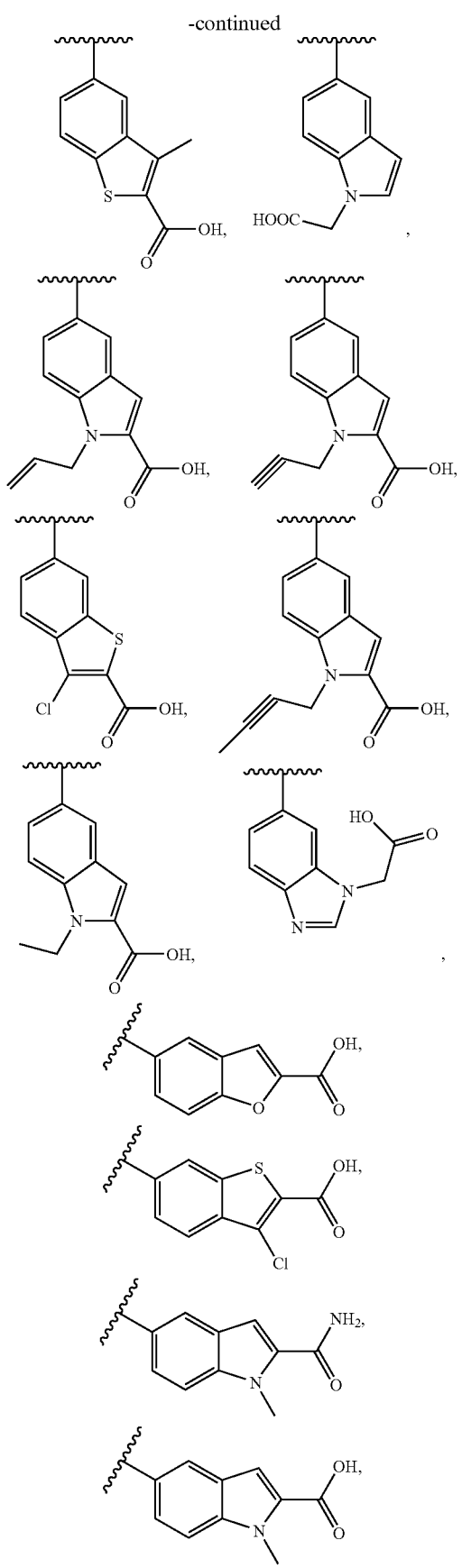
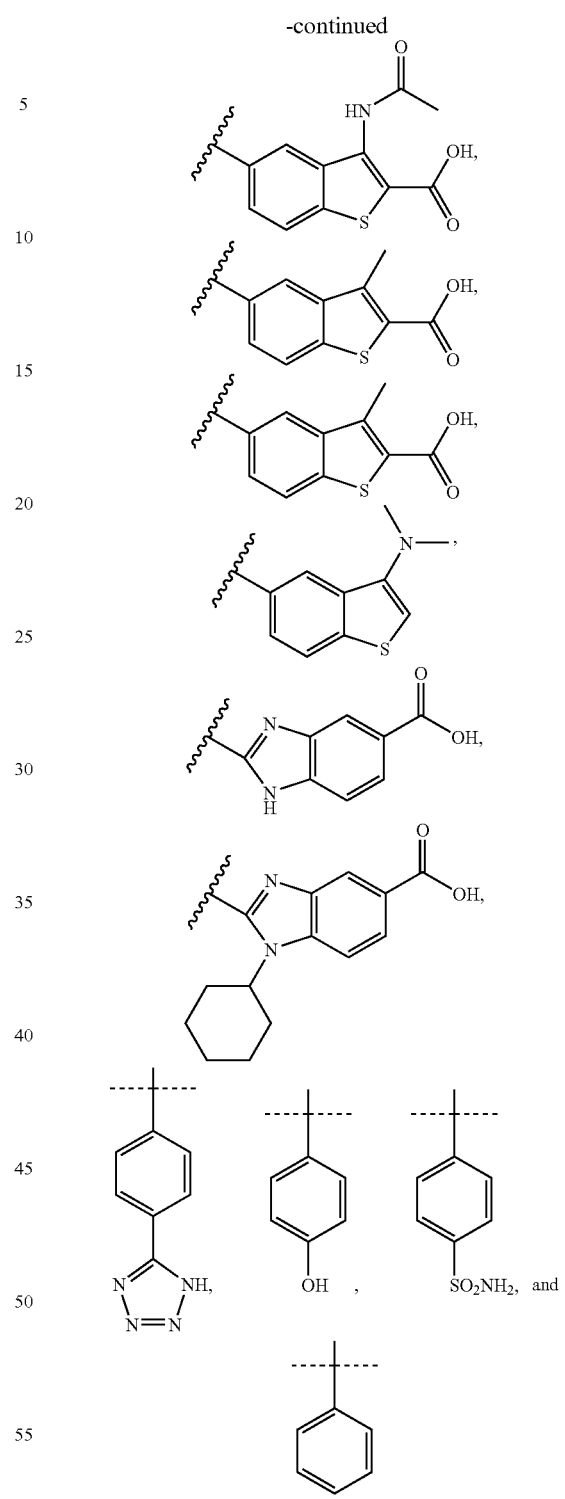
in the presence of:
- a Pd- or Ni-containing catalyst,
- a ligand selected from Ph$_3$P, p-Tol$_3$P, tri(2-furyl)phosphine. Cy$_3$P, tBu$_3$P, Cy$_2$P(Ph-Ph), dppf and dppb, and
- a solvent selected from THF, DMF, NMP or a combination thereof,
at a temperature of between ambient and 100° C.,
to provide the compound of formula I.

2. The process of claim 1 wherein the weight ratio of the compound of formula I is 2.5 fold greater than that that of the corresponding 2H indole product not substituted by Y.

3. The process of claim 1 wherein the catalyst is Pd.

4. The process of claim 1 wherein the ligand is Ph₃P, Cy₃P or Cy₂P(Ph-Ph).

5. The process of claim 1 wherein the solvent is a mixture of THF and NMP.

6. The process of claim 1 for making a compound of formula I
wherein
L is Br or Cl
R is H or methyl;
X is C₃-C₈cycloalkyl;
Y is heteroaryl or aryl;
Z is H, HO₂C—, C₁₋₈alkylO₂C—,

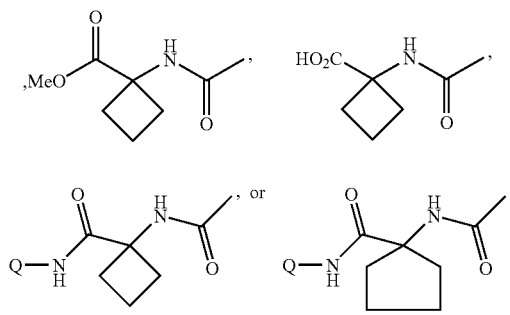

wherein Q is selected from:

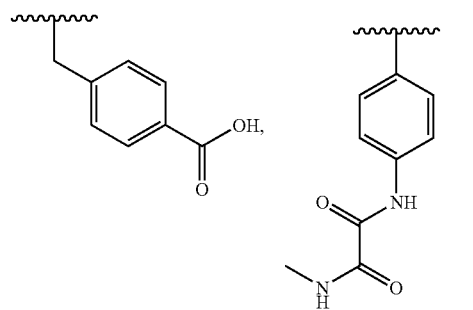

-continued

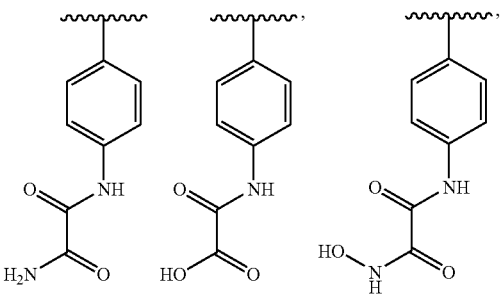

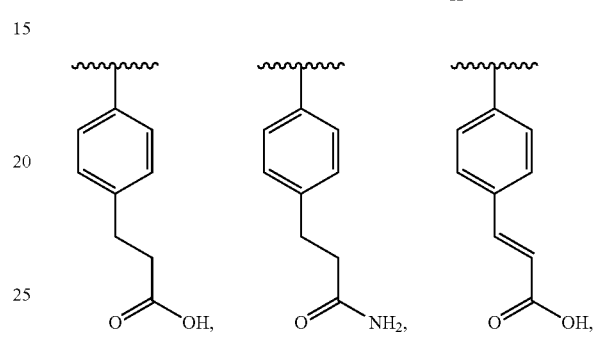

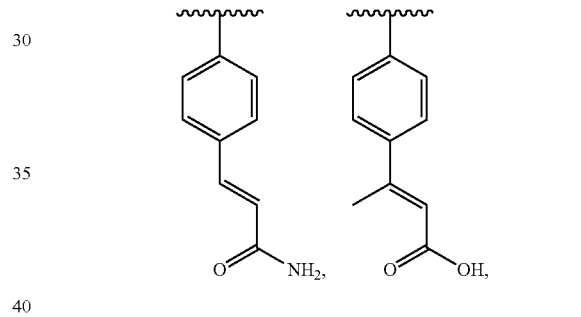

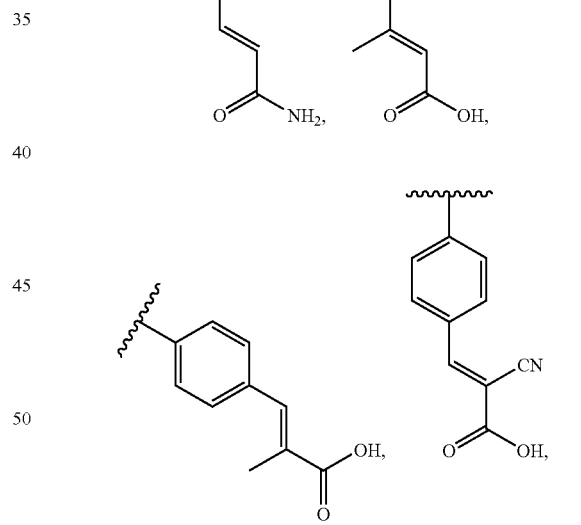

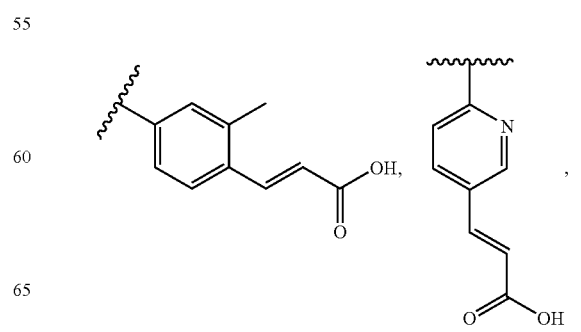

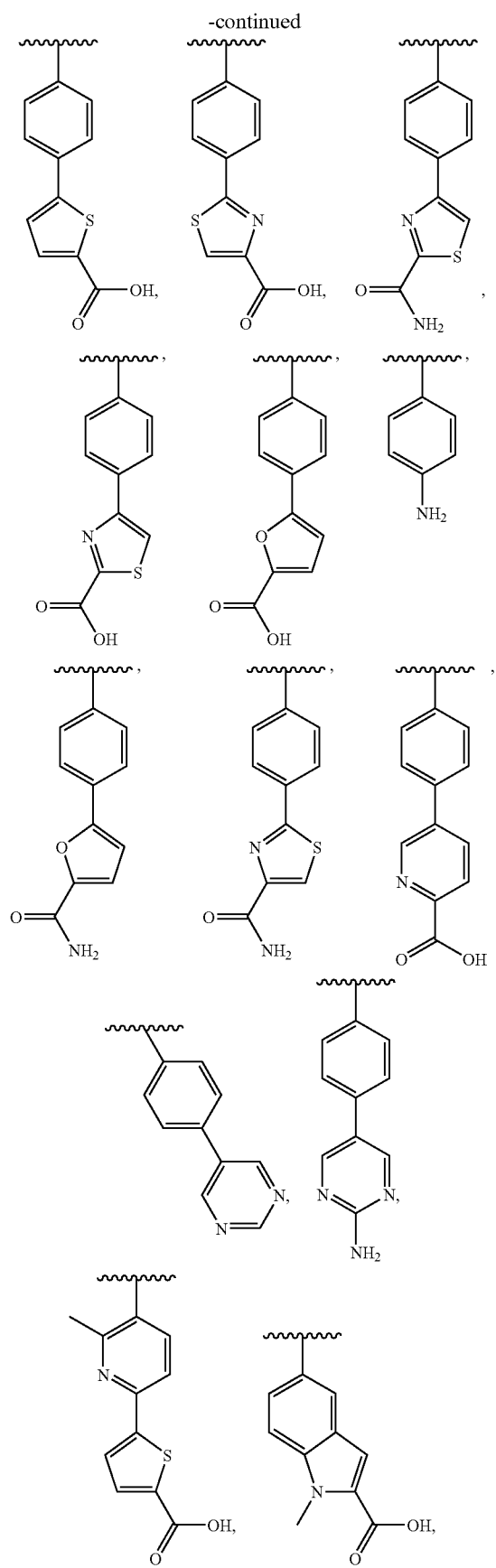
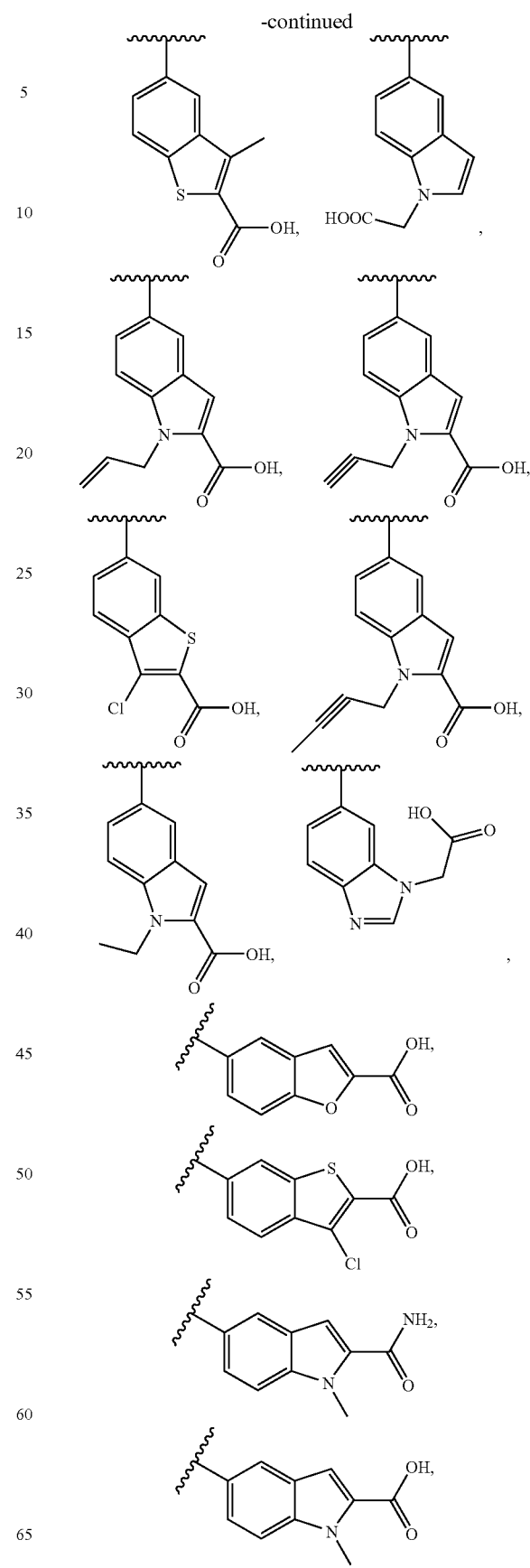

-continued
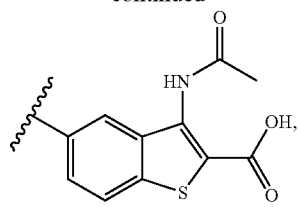
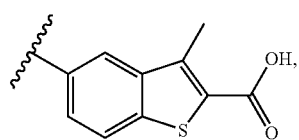
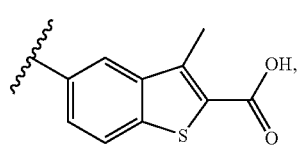
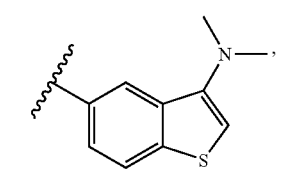
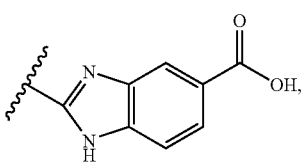
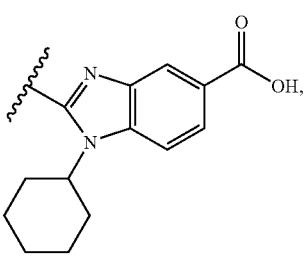
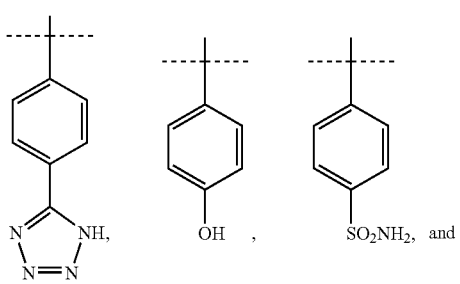
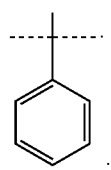
7. The process of claim 1 for making a compound of formula I:
wherein:
L is Br or Cl
R is H or methyl
X is cyclopentyl
Y is pyridyl
L is Br or Cl; and
Z is H, HO$_2$C—, C$_{1-8}$alkylO$_2$C—,
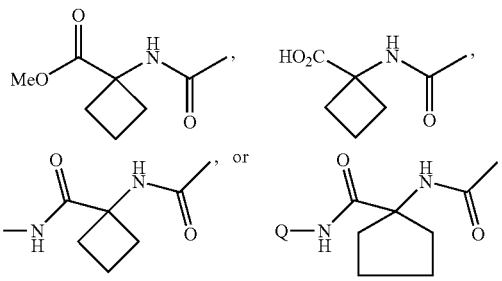
wherein Q is selected from:
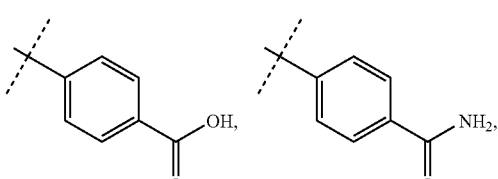
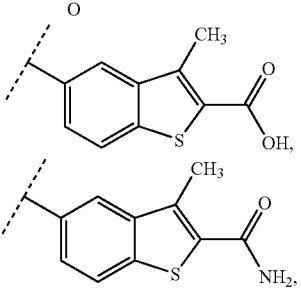
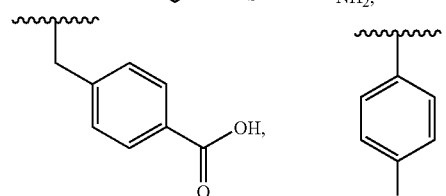
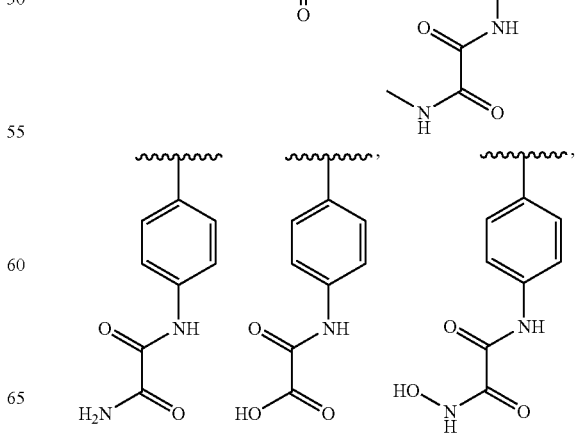

-continued
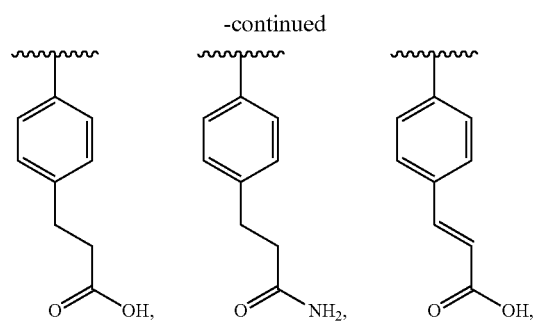
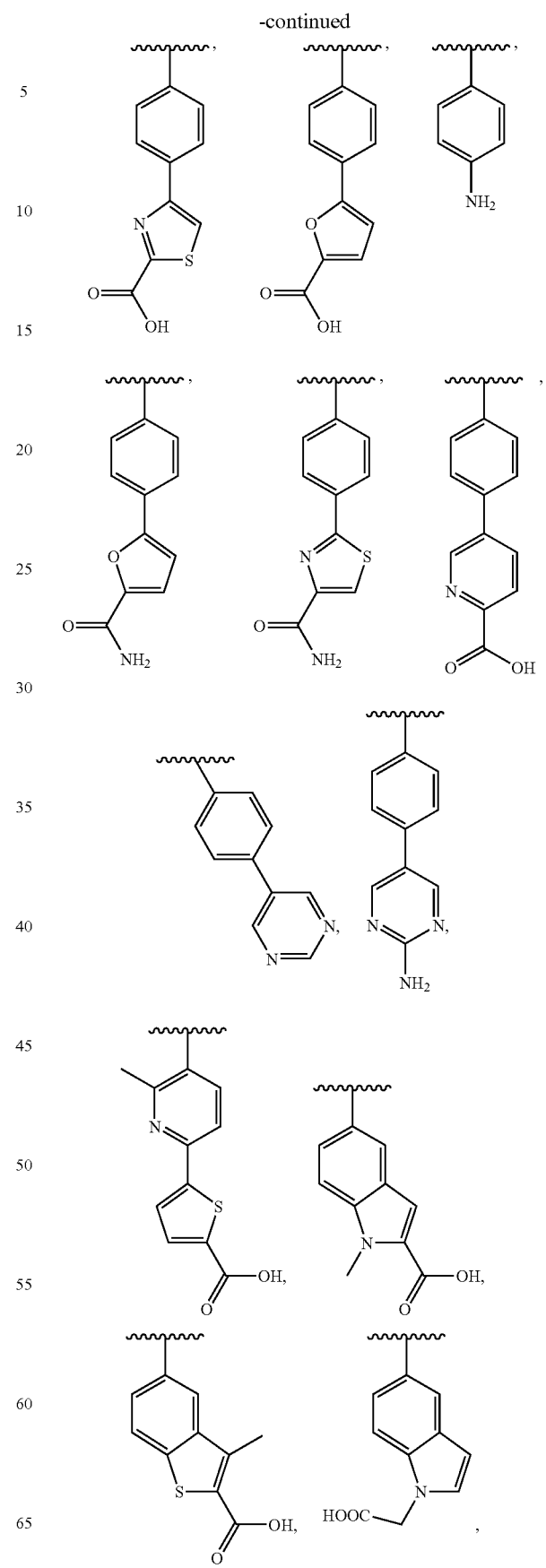

-continued
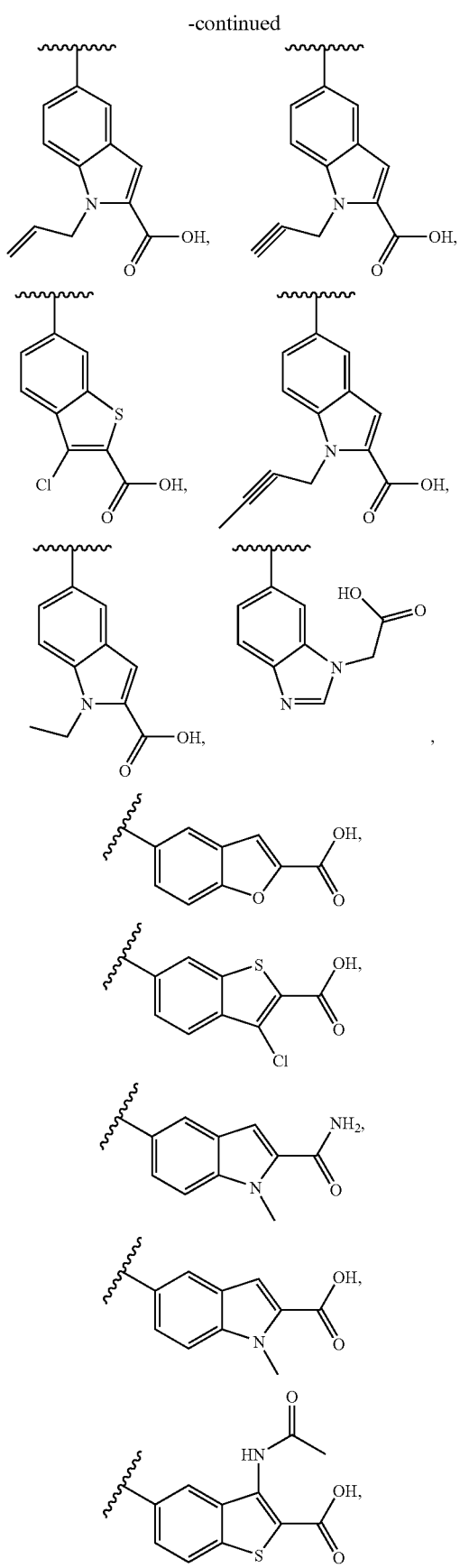
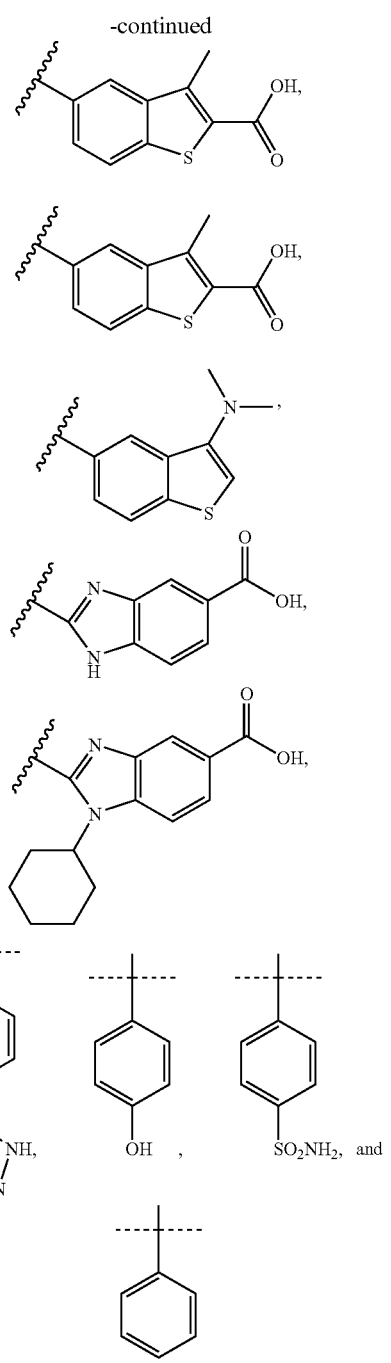
in the presence of:
Pd(OAc)$_2$,
a ligand selected from Ph$_3$P, p-Tol$_3$P, (2-furyl)$_3$P, or Cy$_2$P(Ph-Ph), dppb and Cy$_3$P, and
a 2:1 by volume mixture of NMP to THF, at a temperature between 70° C. and 90° C.
8. The process of claim 1 for making a compound of formula I
wherein:
L is Br or Cl
R is H or methyl, Z is

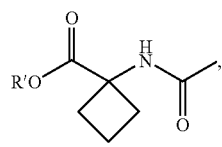

X is cyclopenty,
Y is pyridyl and
R' is H or $C_{1-8}$alkyl,
in the presence of:
Pd(OAc)$_2$,
a ligand selected from Ph$_3$P, p-Tol$_3$P, (2-furyl)$_3$P, dppb and Cy$_2$P(Ph-Ph), and a 2:1 by volume mixture of NMP to THF,
at a temperature between 70° C. and 90° C.

9. The compound having the formula:

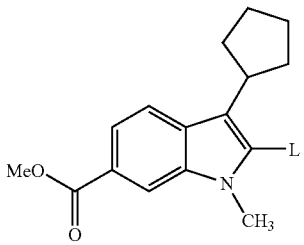

wherein L is Br or Cl.

10. The compound having the formula:

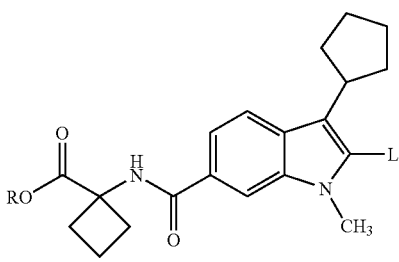

wherein L is Br or Cl; and
R is H or methyl.

11. The process of claim 1 for making a compound of formula I, wherein R is $C_{1-8}$ alkyl.

12. The process of claim 1 for making a compound of formula I, wherein R is methyl.

13. The process of claim 1 for making a compound of formula I, wherein the solvent comprises NMP.

* * * * *